US006303770B1

(12) United States Patent
Lok et al.

(10) Patent No.: US 6,303,770 B1
(45) Date of Patent: Oct. 16, 2001

(54) NUCLEIC ACIDS ENCODING MAMMALIAN ALPHA HELICAL PROTEIN-1

(75) Inventors: Si Lok; Darrell C. Conklin, both of Seattle; Julia E. Parrish, Bainbridge Island, all of WA (US)

(73) Assignee: ZymoGenetics, Inc., Seattle, WA (US)

( * ) Notice: Subject to any disclaimer, the term of this patent is extended or adjusted under 35 U.S.C. 154(b) by 0 days.

(21) Appl. No.: 09/209,525

(22) Filed: Dec. 10, 1998

Related U.S. Application Data

(60) Provisional application No. 60/067,779, filed on Dec. 10, 1997.

(51) Int. Cl.[7] .................................................. C07H 21/04
(52) U.S. Cl. ..................... 536/23.5; 435/320.1; 530/350
(58) Field of Search ........................ 536/23.5; 435/320.1; 530/350

(56) References Cited

FOREIGN PATENT DOCUMENTS

WO 93 05169   3/1993 (WO).

OTHER PUBLICATIONS

EST 335108, GenBank Acc: D60121, Aug. 28, 1995.
EST from Incyte Pharmaceuticals, Inc., 687648, Jan. 4, 1996.
EST from Incyte Pharmaceuticals, Inc., 679721, Jan. 4, 1996.
EST from Incyte Pharmaceuticals, Inc., 677770, Jan. 4, 1996.
EST 448931, GenBank Acc: D80863, Feb. 9, 1996.
EST 448932, GenBank Acc: D80864, Feb. 9, 1996.
EST 604098, GenBank Acc: W95878, Jul. 16, 1996.
EST 604184, GenBank Acc: W95915, Jul. 16, 1996.
EST 1030416, GenBank Acc: AA389097, Apr. 23, 1997.
EST 1040259, GenBank Acc: AA398913, Apr. 24, 1997.
EST from Incyte Pharmaceuticals, Inc., 842032, Mar. 5, 1996.
EST from Incyte Pharmaceuticals, Inc., 780971, Mar. 5, 1996.
EST from Incyte Pharmaceuticals, Inc., 781024, Mar. 5, 1996.
EST from Incyte Pharmaceuticals, Inc., 1366777, May 20, 1996.
EST from Incyte Pharmaceuticals, Inc., 1542442, Aug. 7, 1996.
EST from Incyte Pharmaceuticals, Inc., 1604442, Aug. 7, 1996.
EST from Incyte Pharmaceuticals, Inc., 1604518, Aug. 7, 1996.
EST from Incyte Pharmaceuticals, Inc., 1496586, Aug. 7, 1996.
EST from Incyte Pharmaceuticals, Inc., 1595824, Aug. 7, 1996.
EST from Incyte Pharmaceuticals, Inc., 1689027, Aug. 7, 1996.
EST from Incyte Pharmaceuticals, Inc., 1860223, Sep. 11, 1996.
EST from Incyte Pharmaceuticals, Inc., 1998730, Oct. 17, 1996.
EST from Incyte Pharmaceuticals, Inc., 2187322, Nov. 5, 1996.
EST from Incyte Pharmaceuticals, Inc., 2361588, Dec. 9, 1996.
EST from Incyte Pharmaceuticals, Inc., 2343306, Dec. 9, 1996.
EST from Incyte Pharmaceuticals, Inc., 2343767, Dec. 9, 1996.
EST from Incyte Pharmaceuticals, Inc., 2456494, Jan. 22, 1997.
EST from Incyte Pharmaceuticals, Inc., LIN1604518F6, Feb. 28, 1997.
EST from Incyte Pharmaceuticals, Inc., LIN1604518T6, Feb. 28, 1997.
EST from Incyte Pharmaceuticals, Inc., 2640596, Mar. 10, 1997.
EST from Incyte Pharmaceuticals, Inc., 3086460, May 6, 1997.
EST from Incyte Pharmaceuticals, Inc., 1953715, Aug. 7, 1997.
EST from Incyte Pharmaceuticals, Inc., 1949783, Aug. 7, 1997.
EST from Incyte Pharmaceuticals, Inc., 3596277, Sep. 8, 1997.
EST from Incyte Pharmaceuticals, Inc., 3414120, Sep. 8, 1997.
EST from Incyte Pharmaceuticals, Inc., 3618339, Oct. 6, 1997.
Marra et al., The Wash U–HHMI Mouse EST Project, Accession No. AA389097, Jun. 25, 1997.
Hillier et al., The Wash U–Merck EST Project, Accession No. W95915, Jul. 18, 1996.

*Primary Examiner*—Lorraine Spector
*Assistant Examiner*—Eileen B. O'Hara
(74) *Attorney, Agent, or Firm*—Paul G. Lunn, Esq.

(57) ABSTRACT

Novel mammalian alpha helical polypeptides, polynucleotides encoding the polypeptides, and related compositions and methods including antibodies and anti-idiotypic antibodies.

1 Claim, No Drawings

SEQUENCE LISTING

```
<160> NUMBER OF SEQ ID NOS: 56

<210> SEQ ID NO 1
<211> LENGTH: 907
<212> TYPE: DNA
<213> ORGANISM: Homo sapiens
<220> FEATURE:
<221> NAME/KEY: CDS
<222> LOCATION: (95)...(532)
```

-continued

```
<400> SEQUENCE: 1
cctcgtgccg tggacacgca cttcctgcga gggctccgtg cgcaccttgg ccgagccgaa      60
ccgagccgag tcctgtcctt ccaggccgtt cgca atg gtg gat gag ttg gtg ctg     115
                                     Met Val Asp Glu Leu Val Leu
                                       1               5 ctg ctg cac gcg ctc ctg atg cgg cac cgc gcc ctg agc atc gag aac       163
Leu Leu His Ala Leu Leu Met Arg His Arg Ala Leu Ser Ile Glu Asn
         10                  15                  20 agc cag ctc atg gaa cag ctg cgg ctg ctg gtg tgc gag agg gcc agc       211
Ser Gln Leu Met Glu Gln Leu Arg Leu Leu Val Cys Glu Arg Ala Ser
     25                  30                  35 ctg ctg cgc cag gta cgt ccg ccg agc tgc ccg gtg ccc ttc ccc gaa       259
Leu Leu Arg Gln Val Arg Pro Pro Ser Cys Pro Val Pro Phe Pro Glu
 40                  45                  50                  55 acg ttt aat ggc gag agc tcc cgg ctc ccc gag ttt atc gtg cag acg       307
Thr Phe Asn Gly Glu Ser Ser Arg Leu Pro Glu Phe Ile Val Gln Thr
                 60                  65                  70 gcg tct tac atg ctc gtg aac gag aac cga ttc tgc aac gac gcc atg       355
Ala Ser Tyr Met Leu Val Asn Glu Asn Arg Phe Cys Asn Asp Ala Met
             75                  80                  85 aag gtg gca ttc cta atc agc ctc ctc acc ggg gaa gcc gag gag tgg       403
Lys Val Ala Phe Leu Ile Ser Leu Leu Thr Gly Glu Ala Glu Glu Trp
         90                  95                 100 gtg gtg ccc tac atc gag atg gat agc ccc atc cta ggt gat tac cgg       451
Val Val Pro Tyr Ile Glu Met Asp Ser Pro Ile Leu Gly Asp Tyr Arg
    105                 110                 115 gcc ttc ctc gat gag atg aaa cag tgc ttt ggc tgg gat gac gac gaa       499
Ala Phe Leu Asp Glu Met Lys Gln Cys Phe Gly Trp Asp Asp Asp Glu
120                 125                 130                 135 gac gac gac gac gaa gaa gag gag gat gat tat taggccctcg accctcgggc    552
Asp Asp Asp Asp Glu Glu Glu Glu Asp Asp Tyr
                140                 145 ctcgggggggg agggccctgc amgccgccac ccctcccccg cagccctcac ccgccagga     612 gccactgctc tccccttgc cctccggtcc ccttacctac tcggagtgtc ctcccctgcc      672
ccaccagatt gctgcagggg cgcggtgtgc ctggcagcca aattgttgac acttcttttt     732
tcctatgcac tggttttaca cagctgtcat ttttctttca aaattgcagc agtcccacag     792
atgtgtgcat ttggacaaat agtacttaaa aacaaaacaa acaagcactc agcccagctc     852
ctcaatacta cctggaaaaa gcattggcat tattttcaat aaatatcaag cacta          907

<210> SEQ ID NO 2
<211> LENGTH: 146
<212> TYPE: PRT
<213> ORGANISM: Homo sapiens

<400> SEQUENCE: 2

Met Val Asp Glu Leu Val Leu Leu Leu His Ala Leu Leu Met Arg His
  1               5                  10                  15

Arg Ala Leu Ser Ile Glu Asn Ser Gln Leu Met Glu Gln Leu Arg Leu
             20                  25                  30

Leu Val Cys Glu Arg Ala Ser Leu Leu Arg Gln Val Arg Pro Pro Ser
         35                  40                  45

Cys Pro Val Pro Phe Pro Glu Thr Phe Asn Gly Glu Ser Ser Arg Leu
     50                  55                  60

Pro Glu Phe Ile Val Gln Thr Ala Ser Tyr Met Leu Val Asn Glu Asn
 65                  70                  75                  80
```

```
Arg Phe Cys Asn Asp Ala Met Lys Val Ala Phe Leu Ile Ser Leu Leu
                85                  90                  95

Thr Gly Glu Ala Glu Glu Trp Val Val Pro Tyr Ile Glu Met Asp Ser
            100                 105                 110

Pro Ile Leu Gly Asp Tyr Arg Ala Phe Leu Asp Glu Met Lys Gln Cys
            115                 120                 125

Phe Gly Trp Asp Asp Asp Glu Asp Asp Asp Glu Glu Glu Glu Asp
    130                 135                 140

Asp Tyr
145

<210> SEQ ID NO 3
<211> LENGTH: 270
<212> TYPE: DNA
<213> ORGANISM: Homo sapiens

<400> SEQUENCE: 3
cctcgtgccg tggacacgca cttcctgcga gggctccgtg cgcaccttgg ccgagccgaa    60
ccgagccgag tcctgtcctt ccaggccgtt cgcaatggtg gatgagttgg tgctgctgct   120
gcacgcgctc ctgatgcggc accgcgccct gagcatcgag aacagccagc tcatggaaca   180
gctgcggctg ctggtgtgcg agagggccag cctgctgcgc caggtacgtc gccgagctg    240 cccggtgccc ttccccgaaa cgtttaatgg                                    270

<210> SEQ ID NO 4
<211> LENGTH: 18
<212> TYPE: DNA
<213> ORGANISM: Homo sapiens

<400> SEQUENCE: 4
gcagcagtcc cacagatg                                                  18

<210> SEQ ID NO 5
<211> LENGTH: 18
<212> TYPE: DNA
<213> ORGANISM: Homo sapiens

<400> SEQUENCE: 5
tgggctgagt gcttgttt                                                  18

<210> SEQ ID NO 6
<211> LENGTH: 45
<212> TYPE: DNA
<213> ORGANISM: Homo sapiens

<400> SEQUENCE: 6
ctgctgtgtg gcgccgtctt cgtttcgccc agccaggaaa tccat                    45

<210> SEQ ID NO 7
<211> LENGTH: 45
<212> TYPE: DNA
<213> ORGANISM: Homo sapiens

<400> SEQUENCE: 7
tcgcccagcc aggaaatcca tgccgagttc aacgcggcc gtaga                     45

<210> SEQ ID NO 8
<211> LENGTH: 45
<212> TYPE: DNA
<213> ORGANISM: Homo sapiens
```

<400> SEQUENCE: 8
tcgcccagcc aggaaatcca tgccgagttc caacgcggcc gtaga         45

<210> SEQ ID NO 9
<211> LENGTH: 62
<212> TYPE: DNA
<213> ORGANISM: Homo sapiens

<400> SEQUENCE: 9
cagcagccgc agctgttcca tgagctggct gttctcgatt ctacggccgc gttggaactc    60
gg                                                                  62

<210> SEQ ID NO 10
<211> LENGTH: 54
<212> TYPE: DNA
<213> ORGANISM: Homo sapiens

<400> SEQUENCE: 10
tacctggcgc agcaggctgg ccctctcgca caccagcagc cgcagctgtt ccat          54

<210> SEQ ID NO 11
<211> LENGTH: 141
<212> TYPE: DNA
<213> ORGANISM: Homo sapiens

<400> SEQUENCE: 11
ctgctgtgtg gcgccgtctt cgtttcgccc agccaggaaa tccatgccga gttccaacgc    60
ggccgtagaa tcgagaacag ccagctcatg gaacagctgc ggctgctggt gtgcgagagg   120
gccagcctgc tgcgccaggt a                                             141

<210> SEQ ID NO 12
<211> LENGTH: 54
<212> TYPE: DNA
<213> ORGANISM: Homo sapiens

<400> SEQUENCE: 12
gatgagatga acagtgctt tggctgggat gacgacgaag acgacgacga cgaa           54

<210> SEQ ID NO 13
<211> LENGTH: 70
<212> TYPE: DNA
<213> ORGANISM: Homo sapiens

<400> SEQUENCE: 13
gacgaagacg acgacgacga agaagaggag gatgattatt aatctagagg atctggggtg    60
gcatccctgt                                                          70

<210> SEQ ID NO 14
<211> LENGTH: 46
<212> TYPE: DNA
<213> ORGANISM: Homo sapiens

<400> SEQUENCE: 14
caggagaggc actggggagg ggtcacaggg atgccacccc agatcc        46

<210> SEQ ID NO 15
<211> LENGTH: 46
<212> TYPE: DNA
<213> ORGANISM: Homo sapiens

```
<400> SEQUENCE: 15
ggcactggag tggcaacttc cagggccagg agaggcactg gggagg        46

<210> SEQ ID NO 16
<211> LENGTH: 153
<212> TYPE: DNA
<213> ORGANISM: Homo sapiens

<400> SEQUENCE: 16
gatgagatga aacagtgctt tggctgggat gacgacgaag acgacgacga cgaagaagag    60
gaggatgatt attaatctag aggatctggg gtggcatccc tgtgacccct ccccagtgcc   120
tctcctggcc ctggaagttg ccactccagt gcc                                153

<210> SEQ ID NO 17
<211> LENGTH: 45
<212> TYPE: DNA
<213> ORGANISM: Homo sapiens

<400> SEQUENCE: 17
gtttcgccca gccaggaaat ccatgccgag ttccaacgcg gccgt                    45

<210> SEQ ID NO 18
<211> LENGTH: 44
<212> TYPE: DNA
<213> ORGANISM: Homo sapiens

<400> SEQUENCE: 18
ccgagttcca acgcggccgt agagaggagt atatgcctat ggag                     44

<210> SEQ ID NO 19
<211> LENGTH: 66
<212> TYPE: DNA
<213> ORGANISM: Homo sapiens

<400> SEQUENCE: 19
cagcagccgc agctgttcca tgagctggct gttctcgatc tccataggca tatactcctc    60
tctacg                                                               66

<210> SEQ ID NO 20
<211> LENGTH: 141
<212> TYPE: DNA
<213> ORGANISM: Homo sapiens

<400> SEQUENCE: 20
gtttcgccca gccaggaaat ccatgccgag ttccaacgcg gccgtagaga ggagtatatg    60
cctatggaga tcgagaacag ccagctcatg gaacagctgc ggctgctggt gtgcgagagg   120
gccagcctgc tgcgccaggt a                                              141

<210> SEQ ID NO 21
<211> LENGTH: 63
<212> TYPE: DNA
<213> ORGANISM: Homo sapiens

<400> SEQUENCE: 21
gacgaagacg acgacgacga agaagaggag gatgattatg aagaatacat gcccatggaa    60
taa                                                                  63

<210> SEQ ID NO 22
<211> LENGTH: 46
```

-continued

```
<212> TYPE: DNA
<213> ORGANISM: Homo sapiens

<400> SEQUENCE: 22
atgccacccc agatcctcta gattattcca tgggcatgta ttcttc              46

<210> SEQ ID NO 23
<211> LENGTH: 45
<212> TYPE: DNA
<213> ORGANISM: Homo sapiens

<400> SEQUENCE: 23
ggcactgggg aggggtcaca gggatgccac cccagatcct ctaga               45

<210> SEQ ID NO 24
<211> LENGTH: 141
<212> TYPE: DNA
<213> ORGANISM: Homo sapiens

<400> SEQUENCE: 24
gatgagatga aacagtgctt tggctgggat gacgacgaag acgacgacga cgaagaagag    60
gaggatgatt atgaagaata catgcccatg gaataatcta gaggatctgg ggtggcatcc   120
ctgtgacccc tccccagtgc c                                            141

<210> SEQ ID NO 25
<211> LENGTH: 7
<212> TYPE: PRT
<213> ORGANISM: Homo sapiens

<400> SEQUENCE: 25

Glu Glu Tyr Met Pro Met Glu
 1               5

<210> SEQ ID NO 26
<211> LENGTH: 30
<212> TYPE: DNA
<213> ORGANISM: Homo sapiens

<400> SEQUENCE: 26
cgtaatacga ctcactatag ggcgaattgg                                    30

<210> SEQ ID NO 27
<211> LENGTH: 27
<212> TYPE: DNA
<213> ORGANISM: Homo sapiens

<400> SEQUENCE: 27
gaaacagcta tgaccatgat tacgcca                                       27

<210> SEQ ID NO 28
<211> LENGTH: 44
<212> TYPE: DNA
<213> ORGANISM: Homo sapiens

<400> SEQUENCE: 28
agcattgctg ctaaagaaga aggtgtaagc ttggacaaga gaga                    44

<210> SEQ ID NO 29
<211> LENGTH: 51
<212> TYPE: DNA
<213> ORGANISM: Homo sapiens

<400> SEQUENCE: 29
```

-continued

```
ggtgtaagct tggacaagag agaagaagaa tacatgccaa tggaaggtgg t            51

<210> SEQ ID NO 30
<211> LENGTH: 63
<212> TYPE: DNA
<213> ORGANISM: Homo sapiens

<400> SEQUENCE: 30
cagcagccgc agctgttcca tcagctggct gttctcgata ccaccttcca ttggcatgta   60
ttc                                                                 63

<210> SEQ ID NO 31
<211> LENGTH: 52
<212> TYPE: DNA
<213> ORGANISM: Homo sapiens

<400> SEQUENCE: 31
atcatagaag agaaaaacat tagttggcaa actctcaaaa attataaaaa ta           52

<210> SEQ ID NO 32
<211> LENGTH: 51
<212> TYPE: DNA
<213> ORGANISM: Homo sapiens

<400> SEQUENCE: 32
tggcaaactc tcaaaaatta taaaaatatc caaacaggca gccgaattct a            51

<210> SEQ ID NO 33
<211> LENGTH: 62
<212> TYPE: DNA
<213> ORGANISM: Homo sapiens

<400> SEQUENCE: 33
gacgaagacg acgacgacga agaagaggag gatgattatt agaattcggc tgcctgtttg   60
ga                                                                  62

<210> SEQ ID NO 34
<211> LENGTH: 55
<212> TYPE: DNA
<213> ORGANISM: Homo sapiens

<400> SEQUENCE: 34
gatgagatga aacagtgctt tggctgggat gacgacgaag acgacgacga cgaag        55

<210> SEQ ID NO 35
<211> LENGTH: 144
<212> TYPE: DNA
<213> ORGANISM: Homo sapiens

<400> SEQUENCE: 35
agcattgctg ctaaagaaga aggtgtaagc ttggacaaga gagaagaaga atacatgcca   60
atggaaggtg gtatcgagaa cagccagctc atggaacagc tgcggctgct ggtgtgcgag  120
agggccagcc tgctgcgcca ggta                                         144

<210> SEQ ID NO 36
<211> LENGTH: 147
<212> TYPE: DNA
<213> ORGANISM: Homo sapiens

<400> SEQUENCE: 36
```
gatgagatga aacagtgctt tggctgggat gacgacgaag acgacgacga cgaagaagag    60
gaggatgatt attagaattc ggctgcctgt ttggatattt ttataatttt tgagagtttg   120
ccaactaatg tttttctctt ctatgat                                       147

<210> SEQ ID NO 37
<211> LENGTH: 40
<212> TYPE: DNA
<213> ORGANISM: Homo sapiens

<400> SEQUENCE: 37 acgtttatt gtttatcaat actactattg ctagcattgc                           40

<210> SEQ ID NO 38
<211> LENGTH: 62
<212> TYPE: DNA
<213> ORGANISM: Homo sapiens

<400> SEQUENCE: 38
tcaatactac tattgctagc attgctgcta aagaagaagg tgtaagcttg gacaagagag    60
aa                                                                   62

<210> SEQ ID NO 39
<211> LENGTH: 63
<212> TYPE: DNA
<213> ORGANISM: Homo sapiens

<400> SEQUENCE: 39
cagcagccgc agctgttcca tgagctggct gttctcgatt tctctcttgt ccaagcttac    60
acc                                                                  63

<210> SEQ ID NO 40
<211> LENGTH: 144
<212> TYPE: DNA
<213> ORGANISM: Homo sapiens

<400> SEQUENCE: 40
ttattgttta tcaatactac tattgctagc attgctgcta aagaagaagg tgtaagcttg    60
gacaagagag aaatcgagaa cagccagctc atggaacagc tgcggctgct ggtgtgcgag   120
agggccagcc tgctgcgcca ggta                                          144

<210> SEQ ID NO 41
<211> LENGTH: 39
<212> TYPE: DNA
<213> ORGANISM: Homo sapiens

<400> SEQUENCE: 41
attataaaaa tatccaaaca ggcagcccta gaatactag                           39

<210> SEQ ID NO 42
<211> LENGTH: 58
<212> TYPE: DNA
<213> ORGANISM: Homo sapiens

<400> SEQUENCE: 42
aacaggcagc cctagaatac taggaattct actccatagg catatactcc tcgcctcc      58

<210> SEQ ID NO 43
<211> LENGTH: 61
<212> TYPE: DNA
<213> ORGANISM: Homo sapiens

<400> SEQUENCE: 43
gacgaagacg acgacgacga agaagaggag gatgattatg gaggcgagga gtatatgcct        60
a                                                                        61

<210> SEQ ID NO 44
<211> LENGTH: 144
<212> TYPE: DNA
<213> ORGANISM: Homo sapiens

<400> SEQUENCE: 44
gatgagatga aacagtgctt tggctgggat gacgacgaag acgacgacga cgaagaagag        60
gaggatgatt atgaggcgag ggagtatatg cctatggagt agaattccta gtattctagg       120
gctgcctgtt tggatatttt tata                                              144

<210> SEQ ID NO 45
<211> LENGTH: 126
<212> TYPE: PRT
<213> ORGANISM: Homo sapiens

<400> SEQUENCE: 45

Ile Glu Asn Ser Gln Leu Met Glu Gln Leu Arg Leu Leu Val Cys Glu
 1               5                  10                  15

Arg Ala Ser Leu Leu Arg Gln Val Arg Pro Pro Ser Cys Pro Val Pro
                20                  25                  30

Phe Pro Glu Thr Phe Asn Gly Glu Ser Ser Arg Leu Pro Glu Phe Ile
            35                  40                  45

Val Gln Thr Ala Ser Tyr Met Leu Val Asn Glu Asn Arg Phe Cys Asn
        50                  55                  60

Asp Ala Met Lys Val Ala Phe Leu Ile Ser Leu Leu Thr Gly Glu Ala
    65                  70                  75                  80

Glu Glu Trp Val Val Pro Tyr Ile Glu Met Asp Ser Pro Ile Leu Gly
                85                  90                  95

Asp Tyr Arg Ala Phe Leu Asp Glu Met Lys Gln Cys Phe Gly Trp Asp
               100                 105                 110

Asp Asp Glu Asp Asp Asp Asp Glu Glu Glu Asp Asp Tyr
           115                 120                 125

<210> SEQ ID NO 46
<211> LENGTH: 15
<212> TYPE: PRT
<213> ORGANISM: Homo sapiens

<400> SEQUENCE: 46

Asn Ser Gln Leu Met Glu Gln Leu Arg Leu Leu Val Cys Glu Arg
 1               5                  10                  15

<210> SEQ ID NO 47
<211> LENGTH: 15
<212> TYPE: PRT
<213> ORGANISM: Homo sapiens

<400> SEQUENCE: 47

Phe Pro Glu Thr Phe Asn Gly Glu Ser Ser Arg Leu Pro Glu Phe
 1               5                  10                  15

<210> SEQ ID NO 48
<211> LENGTH: 15
<212> TYPE: PRT

-continued

```
<213> ORGANISM: Homo sapiens

<400> SEQUENCE: 48

Phe Cys Asn Asp Ala Met Lys Val Ala Phe Leu Ile Ser Leu Leu
1               5                   10                  15

<210> SEQ ID NO 49
<211> LENGTH: 15
<212> TYPE: PRT
<213> ORGANISM: Homo sapiens

<400> SEQUENCE: 49

Tyr Arg Ala Phe Leu Asp Glu Met Lys Gln Cys Phe Gly Trp Asp
1               5                   10                  15

<210> SEQ ID NO 50
<211> LENGTH: 45
<212> TYPE: PRT
<213> ORGANISM: Homo sapiens

<400> SEQUENCE: 50

Asn Ser Gln Leu Met Glu Gln Leu Arg Leu Leu Val Cys Glu Arg Ala
1               5                   10                  15

Ser Leu Leu Arg Gln Val Arg Pro Pro Ser Cys Pro Val Pro Phe Pro
                20                  25                  30

Glu Thr Phe Asn Gly Glu Ser Ser Arg Leu Pro Glu Phe
            35                  40                  45

<210> SEQ ID NO 51
<211> LENGTH: 74
<212> TYPE: PRT
<213> ORGANISM: Homo sapiens

<400> SEQUENCE: 51

Asn Ser Gln Leu Met Glu Gln Leu Arg Leu Leu Val Cys Glu Arg Ala
1               5                   10                  15

Ser Leu Leu Arg Gln Val Arg Pro Pro Ser Cys Pro Val Pro Phe Pro
                20                  25                  30

Glu Thr Phe Asn Gly Glu Ser Ser Arg Leu Pro Glu Phe Ile Val Gln
            35                  40                  45

Thr Ala Ser Tyr Met Leu Val Asn Glu Asn Arg Phe Cys Asn Asp Ala
        50                  55                  60

Met Lys Val Ala Phe Leu Ile Ser Leu Leu
65                  70

<210> SEQ ID NO 52
<211> LENGTH: 110
<212> TYPE: PRT
<213> ORGANISM: Homo sapiens

<400> SEQUENCE: 52

Asn Ser Gln Leu Met Glu Gln Leu Arg Leu Leu Val Cys Glu Arg Ala
1               5                   10                  15

Ser Leu Leu Arg Gln Val Arg Pro Pro Ser Cys Pro Val Pro Phe Pro
                20                  25                  30

Glu Thr Phe Asn Gly Glu Ser Ser Arg Leu Pro Glu Phe Ile Val Gln
            35                  40                  45

Thr Ala Ser Tyr Met Leu Val Asn Glu Asn Arg Phe Cys Asn Asp Ala
        50                  55                  60

Met Lys Val Ala Phe Leu Ile Ser Leu Leu Thr Gly Glu Ala Glu Glu
```

-continued

```
                65                  70                  75                  80
Trp Val Val Pro Tyr Ile Glu Met Asp Ser Pro Ile Leu Gly Asp Tyr
                    85                  90                  95

Arg Ala Phe Leu Asp Glu Met Lys Gln Cys Phe Gly Trp Asp
                100                 105                 110

<210> SEQ ID NO 53
<211> LENGTH: 44
<212> TYPE: PRT
<213> ORGANISM: Homo sapiens

<400> SEQUENCE: 53

Phe Pro Glu Thr Phe Asn Gly Glu Ser Ser Arg Leu Pro Glu Phe Ile
 1               5                  10                  15

Val Gln Thr Ala Ser Tyr Met Leu Val Asn Glu Asn Arg Phe Cys Asn
                20                  25                  30

Asp Ala Met Lys Val Ala Phe Leu Ile Ser Leu Leu
                35                  40

<210> SEQ ID NO 54
<211> LENGTH: 80
<212> TYPE: PRT
<213> ORGANISM: Homo sapiens

<400> SEQUENCE: 54

Phe Pro Glu Thr Phe Asn Gly Glu Ser Ser Arg Leu Pro Glu Phe Ile
 1               5                  10                  15

Val Gln Thr Ala Ser Tyr Met Leu Val Asn Glu Asn Arg Phe Cys Asn
                20                  25                  30

Asp Ala Met Lys Val Ala Phe Leu Ile Ser Leu Leu Thr Gly Glu Ala
                35                  40                  45

Glu Glu Trp Val Val Pro Tyr Ile Glu Met Asp Ser Pro Ile Leu Gly
            50                  55                  60

Asp Tyr Arg Ala Phe Leu Asp Glu Met Lys Gln Cys Phe Gly Trp Asp
65                  70                  75                  80

<210> SEQ ID NO 55
<211> LENGTH: 51
<212> TYPE: PRT
<213> ORGANISM: Homo sapiens

<400> SEQUENCE: 55

Phe Cys Asn Asp Ala Met Lys Val Ala Phe Leu Ile Ser Leu Leu Thr
 1               5                  10                  15

Gly Glu Ala Glu Glu Trp Val Val Pro Tyr Ile Glu Met Asp Ser Pro
                20                  25                  30

Ile Leu Gly Asp Tyr Arg Ala Phe Leu Asp Glu Met Lys Gln Cys Phe
                35                  40                  45

Gly Trp Asp
        50

<210> SEQ ID NO 56
<211> LENGTH: 65
<212> TYPE: PRT
<213> ORGANISM: Homo sapiens

<400> SEQUENCE: 56

Phe Cys Asn Asp Ala Met Lys Val Ala Phe Leu Ile Ser Leu Leu Thr
 1               5                  10                  15
```

```
Gly Glu Ala Glu Glu Trp Val Val Pro Tyr Ile Glu Met Asp Ser Pro
         20                  25                  30

Ile Leu Gly Asp Tyr Arg Ala Phe Leu Asp Glu Met Lys Gln Cys Phe
         35                  40                  45

Gly Trp Asp Asp Asp Glu Asp Asp Asp Glu Glu Glu Asp Asp
     50                  55                  60

Tyr
65
```

NUCLEIC ACIDS ENCODING MAMMALIAN ALPHA HELICAL PROTEIN-1

The present application is a 35 U.S.C. §111(a) application which claims priority under 35 U.S.C. §119(e) to provisional patent application No. 60/067,779 filed Dec. 10, 1997.

BACKGROUND OF THE INVENTION

Proliferation, maintenance, survival and differentiation of cells of multicellular organisms are controlled by hormones and polypeptide growth factors. These diffusable molecules allow cells to communicate with each other and act in concert to form cells and organs, and to repair and regenerate damaged tissue. Examples of hormones and growth factors include the steroid hormones (e.g. estrogen, testosterone), parathyroid hormone, follicle stimulating hormone, the interleukins, platelet derived growth factor (PDGF), epidermal growth factor (EGF), granulocyte-macrophage colony stimulating factor (GM-CSF), erythropoietin (EPO) and calcitonin.

Hormones and growth factors influence cellular metabolism by binding to proteins. Proteins may be integral membrane proteins that are linked to signaling pathways within the cell, such as second messenger systems. Other classes of proteins are soluble molecules, such as the transcription factors.

Of particular interest are cytokines, molecules that promote the proliferation, maintenance, survival or differentiation of cells. Examples of cytokines include erythropoietin (EPO), which stimulates the development of red blood cells; thrombopoietin (TPO), which stimulates development of cells of the megakaryocyte lineage; and granulocyte-colony stimulating factor (G-CSF), which stimulates development of neutrophils. These cytokines are useful in restoring normal blood cell levels in patients suffering from anemia or receiving chemotherapy for cancer. The demonstrated in vivo activities of these cytokines illustrates the enormous clinical potential of, and need for, other cytokines, cytokine agonists, and cytokine antagonists.

SUMMARY OF THE INVENTION

The present invention addresses this need by providing a novel polypeptide and related compositions and methods. Within one aspect, the present invention provides an isolated polynucleotide encoding a mammalian protein termed "Alpha helical protein-1" or Zalpha1. The human Zalpha1 polypeptide is comprised of a sequence of amino acids 146 amino acids long with the initial Met as shown in SEQ ID NO:1 and SEQ ID NO:2. It is believed that amino residues 1–20 are signal sequence, and the mature Zalpha1 polypeptide is represented by the amino acid sequence comprised residues 21, an isoleucine, through amino acid residue 146, a tyrosine. The mature Zalpha1 polypeptide is also defined by SEQ ID NO:45. Within an additional embodiment, the polypeptide further comprises an affinity tag. Within a further embodiment, the polynucleotide is DNA.

Also claimed are polypeptides which are at least 90% identical to SEQ ID NO:2 or SEQ ID NO:45 and polynucleotides which encode the polypeptides.

Within a second aspect of the invention there is provided an expression vector comprising (a) a transcription promoter; (b) a DNA segment encoding a Zalpha1 polypeptide, and (c) a transcription terminator, wherein the promoter, DNA segment, and terminator are operably linked.

Within a third aspect of the invention there is provided a cultured eukaryotic or bacterial cell into which has been introduced an expression vector as disclosed above, wherein said cell expresses a Zalpha1 polypeptide encoded by the DNA segment.

Within a further aspect of the invention there is provided a chimeric polypeptide consisting essentially of a first portion and a second portion joined by a peptide bond. The first portion of the chimeric polypeptide is either (a) a Zalpha1 polypeptide as shown in SEQ ID NO: 2 or SEQ ID NO:45 or (b) protein polypeptides that are at least 90% identical to SEQ ID NO:2 or SEQ ID NO:45. The second portion of the chimeric polypeptide consists essentially of another polypeptide such as an affinity tag. Within one embodiment the affinity tag is an immunoglobulin $F_c$ polypeptide. The invention also provides expression vectors encoding the chimeric polypeptides and host cells transfected to produce the chimeric polypeptides.

An additional embodiment of the present invention relates to a peptide or polypeptide which has the amino acid sequence of an epitope-bearing portion of a Zalpha1 polypeptide having an amino acid sequence described above. Peptides or polypeptides having the amino acid sequence of an epitope-bearing portion of a Zalpha1 polypeptide of the present invention include portions of such polypeptides with at least nine, preferably at least 15 and more preferably at least 30 to 50 amino acids, although epitope-bearing polypeptides of any length up to and including the entire amino acid sequence of a polypeptide of the present invention described above are also included in the present invention. Also claimed are any of these polypeptides that are fused to another polypeptide or carrier molecule. Also claimed are any of these polypeptides that are fused to another polypeptide or carrier molecule. Antibodies produced from these epitope-bearing portions of Zalpha1 can be used in purifying Zalpha1 from cell culture medium. Examples of such epitope-bearing polypeptides are the polypeptides of SEQ ID NOs: 46–56. Also claimed are proteins or polypeptide which contain a sequence which is at least 90% identical to an epitope-bearing polypeptide described above.

Within an additional aspect of the invention there is provided an antibody that specifically binds to a Zalpha1 polypeptide as disclosed above, and also an anti-idiotypic antibody which neutralizes the antibody to a Zalpha1 polypeptide.

These and other aspects of the invention will become evident upon reference to the following detailed description.

DETAILED DESCRIPTION OF THE INVENTION

The term "allelic variant" is used herein to denote any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The term "expression vector" is used to denote a DNA molecule, linear or circular, that comprises a segment encoding a polypeptide of interest operably linked to additional segments that provide for its transcription. Such additional segments include promoter and terminator sequences, and may also include one or more origins of replication, one or more selectable markers, an enhancer, a polyadenylation signal, etc. Expression vectors are generally derived from plasmid or viral DNA, or may contain elements of both.

The term "isolated", when applied to a polynucleotide, denotes that the polynucleotide has been removed from its natural genetic milieu and is thus free of other extraneous or unwanted coding sequences, and is in a form suitable for use within genetically engineered protein production systems.

"Operably linked", when referring to DNA segments, indicates that the segments are arranged so that they function in concert for their intended purposes, e.g. transcription initiates in the promoter and proceeds through the coding segment to the terminator.

A "polynucleotide" is a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules.

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes.

A "soluble protein" is a protein polypeptide that is not bound to a cell membrane.

Within preferred embodiments of the invention the isolated polynucleotides will hybridize to similar sized regions of SEQ ID NO:1, or a sequence complementary thereto, under stringent conditions. In general, stringent conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Typical stringent conditions are those in which the salt concentration is about 0.02 M or less at pH 7 and the temperature is at least about 60° C. As previously noted, the isolated polynucleotides of the present invention include DNA and RNA. Methods for isolating DNA and RNA are well known in the art. Total RNA can be prepared using guanidine HCl extraction followed by isolation by centrifugation in a CsCl gradient [Chirgwin et al., *Biochemistry* 18:52–94 (1979)]. Poly (A)$^+$ RNA is prepared from total RNA using the method of Aviv and Leder [*Proc. Natl. Acad. Sci. USA* 69:1408–1412 (1972)]. Complementary DNA (cDNA) is prepared from poly(A)$^+$ RNA using known methods. Polynucleotides encoding Zalpha1 polypeptides are then identified and isolated by, for example, hybridization or PCR.

Additionally, the polynucleotides of the present invention can be synthesized using a DNA synthesizer. Currently the method of choice is the phosphoramidite method. If chemically synthesized double stranded DNA is required for an application such as the synthesis of a gene or a gene fragment, then each complementary strand is made separately. The production of short genes (60 to 80 bp) is technically straightforward and can be accomplished by synthesizing the complementary strands and then annealing them. For the production of longer genes (>300 bp), however, special strategies must be invoked, because the coupling efficiency of each cycle during chemical DNA synthesis is seldom 100%. To overcome this problem, synthetic genes (double-stranded) are assembled in modular form from single-stranded fragments that are from 20 to 100 nucleotides in length. See Glick, Bernard R. and Jack J. Pasternak, *Molecular Biotechnology, Principles & Applications of Recombinant DNA,* (ASM Press, Washington, D.C. 1994), Itakura, K. et al. Synthesis and use of synthetic oligonucleotides. *Annu. Rev. Biochem.* 53 : 323–356 (1984), and Climie, S. et al. Chemical synthesis of the thymidylate synthase gene. *Proc. Natl. Acad. Sci. USA* 87 :633–637 (1990).

Those skilled in the art will recognize that the sequences disclosed in SEQ ID NOS:1, and 2 represent a single allele of the human. Allelic variants of these sequences can be cloned by probing cDNA or genomic libraries from different individuals according to standard procedures.

The present invention further provides counterpart proteins and polynucleotides from other species ("species orthologs"). Of particular interest are Zalpha1 polypeptides from other mammalian species, including murine, porcine, ovine, bovine, canine, feline, equine, and other primates. Species orthologs of the human Zalpha1 protein can be cloned using information and compositions provided by the present invention in combination with conventional cloning techniques. For example, a cDNA can be cloned using mRNA obtained from a tissue or cell type that expresses the protein. Suitable sources of mRNA can be identified by probing Northern blots with probes designed from the sequences disclosed herein. A library is then prepared from mRNA of a positive tissue or cell line. A protein-encoding cDNA can then be isolated by a variety of methods, such as by probing with a complete or partial human or mouse cDNA or with one or more sets of degenerate probes based on the disclosed sequences. A cDNA can also be cloned using the polymerase chain reaction, or PCR (Mullis, U.S. Pat. No. 4,683,202), using primers designed from the sequences disclosed herein. Within an additional method, the cDNA library can be used to transform or transfect host cells, and expression of the cDNA of interest can be detected with an antibody to the protein. Similar techniques can also be applied to the isolation of genomic clones. As used and claimed the language "an isolated polynucleotide which encodes a polypeptide, said polynucleotide being defined by SEQ ID NO: 2" includes all allelic variants and species orthologs of the polypeptide of SEQ ID NO:2.

The present invention also provides isolated protein polypeptides that are substantially identical to the protein polypeptides of SEQ ID NO: 2 and its species orthologs. By "isolated" is meant a protein or polypeptide that is found in a condition other than its native environment, such as apart from blood and animal tissue. In a preferred form, the isolated polypeptide is substantially free of other polypeptides, particularly other polypeptides of animal origin. It is preferred to provide the polypeptides in a highly purified form, i.e. greater than 95% pure, more preferably greater than 99% pure. The term "substantially identical" is used herein to denote polypeptides having 50%, preferably 60%, more preferably at least 80%, sequence identity to the sequence shown in SEQ ID NO:2 or SEQ ID NO:45, or their species orthologs. Such polypeptides will more preferably be at least 90% identical, and most preferably 95% or more identical to SEQ ID NO:2 or SEQ ID NO:45,or their species orthologs. Percent sequence identity is determined by conventional methods. See, for example, Altschul et al., *Bull. Math. Bio.* 48: 603–616, 1986 and Henikoff and Henikoff, *Proc. Natl. Acad. Sci. USA* 89:10915–10919, 1992. Briefly, two amino acid sequences are aligned to optimize the alignment scores using a gap opening penalty of 10, a gap extension penalty of 1, and the "BLOSUM 62" scoring matrix of Henikoff and Henikoff (ibid.) as shown in Table 1 (amino acids are indicated by the standard one-letter codes). The percent identity is then calculated as:

Total number of identical matches/×100

[length of the longer sequence plus the number of gaps introduced into the longer sequence in order to align the two sequences]

TABLE 1

| | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | -1 | 5 | | | | | | | | | | | | | | | | | | |
| N | -2 | 0 | 6 | | | | | | | | | | | | | | | | | |
| D | -2 | -2 | 1 | 6 | | | | | | | | | | | | | | | | |
| C | 0 | -3 | -3 | -3 | 9 | | | | | | | | | | | | | | | |
| Q | -1 | 1 | 0 | 0 | -3 | 5 | | | | | | | | | | | | | | |
| E | -1 | 0 | 0 | 2 | -4 | 2 | 5 | | | | | | | | | | | | | |
| G | 0 | -2 | 0 | -1 | -3 | -2 | -2 | 6 | | | | | | | | | | | | |
| H | -2 | 0 | 1 | -1 | -3 | 0 | 0 | -2 | 8 | | | | | | | | | | | |
| I | -1 | -3 | -3 | -3 | -1 | -3 | -3 | -4 | -3 | 4 | | | | | | | | | | |
| L | -1 | -2 | -3 | -4 | -1 | -2 | -3 | -4 | -3 | 2 | 4 | | | | | | | | | |
| K | -1 | 2 | 0 | -1 | -3 | 1 | 1 | -2 | -1 | -3 | -2 | 5 | | | | | | | | |
| M | -1 | -1 | -2 | -3 | -1 | 0 | -2 | -3 | -2 | 1 | 2 | -1 | 5 | | | | | | | |
| F | -2 | -3 | -3 | -3 | -2 | -3 | -3 | -3 | -1 | 0 | 0 | -3 | 0 | 6 | | | | | | |
| P | -1 | -2 | -2 | -1 | -3 | -1 | -1 | -2 | -2 | -3 | -3 | -1 | -2 | -4 | 7 | | | | | |
| S | 1 | -1 | 1 | 0 | -1 | 0 | 0 | 0 | -1 | -2 | -2 | 0 | -1 | -2 | -1 | 4 | | | | |
| T | 0 | -1 | 0 | -1 | -1 | -1 | -1 | -2 | -2 | -1 | -1 | -1 | -1 | -2 | -1 | 1 | 5 | | | |
| W | -3 | -3 | -4 | -4 | -2 | -2 | -3 | -2 | -2 | -3 | -2 | -3 | -1 | 1 | -4 | -3 | -2 | 11 | | |
| Y | -2 | -2 | -2 | -3 | -2 | -1 | -2 | -3 | 2 | -1 | -1 | -2 | -1 | 3 | -3 | -2 | -2 | 2 | 7 | |
| V | 0 | -3 | -3 | -3 | -1 | -2 | -2 | -3 | -3 | 3 | 1 | -2 | 1 | -1 | -2 | -2 | 0 | -3 | -1 | 4 |

Sequence identity of polynucleotide molecules is determined by similar methods using a ratio as disclosed above.

Substantially homologous proteins and polypeptides are characterized as having one or more amino acid substitutions, deletions or additions. These changes are preferably of a minor nature, that is conservative amino acid substitutions (see Table 2) and other substitutions that do not significantly affect the folding or activity of the protein or polypeptide; small deletions, typically of one to about 30 amino acids; and small amino- or carboxyl-terminal extensions, such as an amino-terminal methionine residue, a small linker peptide of up to about 20–25 residues, or a small extension that facilitates purification (an affinity tag), such as a poly-histidine tract, protein A [Nilsson et al., *EMBO J.* 4:1075 (1985); Nilsson et al., *Methods Enzymol.* 198:3 (1991)], glutathione S transferase.

[Smith and Johnson, *Gene* 67:31 (1988)], or other antigenic epitope or binding domain. See, in general Ford et al., *Protein Expression and Purification* 2: 95–107 (1991). DNAs encoding affinity tags are available from commercial suppliers (e.g., Pharmacia Biotech, Piscataway, N.J.).

TABLE 2

Conservative amino acid substitutions

| | |
|---|---|
| Basic: | arginine |
| | lysine |
| | histidine |
| Acidic: | glutamic acid |
| | aspartic acid |
| Polar: | glutamine |
| | asparagine |
| Hydrophobic: | leucine |
| | isoleucine |
| | valine |
| Aromatic: | phenylalanine |
| | tryptophan |
| | tyrosine |
| Small: | glycine |
| | alanine |
| | serine |
| | threonine |
| | methionine |

Essential amino acids in the polypeptides of the present invention can be identified according to procedures known in the art, such as site-directed mutagenesis or alanine-scanning mutagenesis [Cunningham and Wells, *Science* 244, 1081–1085 (1989); Bass et al., *Proc. Natl. Acad. Sci. USA* 88:4498–4502 (1991)]. In the latter technique, single alanine mutations are introduced at every residue in the molecule, and the resultant mutant molecules are tested for biological activity (e.g., ligand binding and signal transduction) to identify amino acid residues that are critical to the activity of the molecule. Sites of ligand-protein interaction can also be determined by analysis of crystal structure as determined by such techniques as nuclear magnetic resonance, crystallography or photoaffinity labeling. See, for example, de Vos et al., *Science* 255:306–312 (1992); Smith et al., *J. Mol. Biol.* 224:899–904 (1992); Wlodaver et al., *FEBS Lett.* 309:59–64 (1992). The identities of essential amino acids can also be inferred from analysis of homologies with related proteins.

Multiple amino acid substitutions can be made and tested using known methods of mutagenesis and screening, such as those disclosed by Reidhaar-Olson and Sauer, *Science* 241:53–57, (1988) or Bowie and Sauer, *Proc. Natl. Acad. Sci. USA* 86:2152–2156 (1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., *Biochem.* 30:10832–10837 (1991); Ladner et al., U.S. Pat. No. 5,223,409; Huse, WIPO Publication WO 92/06204) and region-directed mutagenesis [Derbyshire et al., *Gene* 46:145 (1986); Ner et al., *DNA* 7:127 (1988)].

Mutagenesis methods as disclosed above can be combined with high-throughput screening methods to detect activity of cloned, mutagenized proteins in host cells. Preferred assays in this regard include cell proliferation assays and biosensor-based ligand-binding assays, which are described below. Mutagenized DNA molecules that encode active proteins or portions thereof (e.g., ligand-binding fragments) can be recovered from the host cells and rapidly sequenced using modern equipment. These methods allow the rapid determination of the importance of individual amino acid residues in a polypeptide of interest, and can be applied to polypeptides of unknown structure.

Using the methods discussed above, one of ordinary skill in the art can prepare a variety of polypeptides that are substantially homologous to SEQ ID NO:2 or allelic variants thereof and retain the properties of the wild-type protein. As expressed and claimed herein the language, "a polypeptide as defined by SEQ ID NO: 2" includes all allelic variants and species orthologs of the polypeptide.

Polynucleotides, generally a cDNA sequence, of the present invention encode the above-described polypeptides. A cDNA sequence which encodes a polypeptide of the present invention is comprised of a series of codons, each amino acid residue of the polypeptide being encoded by a codon and each codon being comprised of three nucleotides. The amino acid residues are encoded by their respective codons as follows.

Alanine (Ala) is encoded by GCA, GCC, GCG or GCT;

Cysteine (Cys) is encoded by TGC or TGT;

Aspartic acid (Asp) is encoded by GAC or GAT;

Glutamic acid (Glu) is encoded by GAA or GAG;

Phenylalanine (Phe) is encoded by TTC or TTT;

Glycine (Gly) is encoded by GGA, GGC, GGG or GGT;

Histidine (His) is encoded by CAC or CAT;

Isoleucine (Ile) is encoded by ATA, ATC or ATT;

Lysine (Lys) is encoded by AAA, or AAG;

Leucine (Leu) is encoded by TTA, TTG, CTA, CTC, CTG or CTT;

Methionine (Met) is encoded by ATG;

Asparagine (Asn) is encoded by AAC or AAT;

Proline (Pro) is encoded by CCA, CCC, CCG or CCT;

Glutamine (Gln) is encoded by CAA or CAG;

Arginine (Arg) is encoded by AGA, AGG, CGA, CGC, CGG or CGT;

Serine (Ser) is encoded by AGC, AGT, TCA, TCC, TCG or TCT;

Threonine (Thr) is encoded by ACA, ACC, ACG or ACT;

Valine (Val) is encoded by GTA, GTC, GTG or GTT;

Tryptophan (Trp) is encoded by TGG; and

Tyrosine (Tyr) is encoded by TAC or TAT.

It is to be recognized that according to the present invention, when a cDNA is claimed as described above, it is understood that what is claimed are both the sense strand, the anti-sense strand, and the DNA as double-stranded having both the sense and anti-sense strand annealed together by their respective hydrogen bonds. Also claimed is the messenger RNA (mRNA) which encodes the polypeptides of the present invention, and which mRNA is encoded by the above-described cDNA. A messenger RNA (mRNA) will encode a polypeptide using the same codons as those defined above, with the exception that each thymine nucleotide (T) is replaced by a uracil nucleotide (U).

The protein polypeptides of the present invention, including full-length proteins, protein fragments (e.g. ligand-binding fragments), and fusion polypeptides can be produced in genetically engineered host cells according to conventional techniques. Suitable host cells are those cell types that can be transformed or transfected with exogenous DNA and grown in culture, and include bacteria, fungal cells, and cultured higher eukaryotic cells. Eukaryotic cells, particularly cultured cells of multicellular organisms, are preferred. Techniques for manipulating cloned DNA molecules and introducing exogenous DNA into a variety of host cells are disclosed by Sambrook et al., *Molecular Cloning: A Laboratory Manual,* 2nd ed. (Cold Spring Harbor Laboratory Press, Cold Spring Harbor, N.Y., 1989), and Ausubel et al., ibid.

In general, a DNA sequence encoding a Zalpha1 polypeptide is operably linked to other genetic elements required for its expression, generally including a transcription promoter and terminator, within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a Zalpha1 polypeptide into the secretory pathway of a host cell, a secretory signal sequence (also known as a leader sequence, prepro sequence or pre sequence) is provided in the expression vector. The secretory signal sequence may be that of the protein, or may be derived from another secreted protein (e.g., t-PA) or synthesized de novo. The secretory signal sequence is joined to the Zalpha1 DNA sequence in the correct reading frame. Secretory signal sequences are commonly positioned 5' to the DNA sequence encoding the polypeptide of interest, although certain signal sequences may be positioned elsewhere in the DNA sequence of interest (see, e.g., Welch et al., U.S. Pat. No. 5,037,743; Holland et al., U.S. Pat. No. 5,143,830).

Cultured mammalian cells are preferred hosts within the present invention. Methods for introducing exogenous DNA into mammalian host cells include calcium phosphate-mediated transfection [Wigler et al., *Cell* 14:725 (1978); Corsaro and Pearson, *Somatic Cell Genetics* 7:603, (1981): Graham and Van der Eb, *Virology* 52:456, (1973)], electroporation [Neumann et al., *EMBO J.* 1:841–845, (1982)], DEAE-dextran mediated transfection [Ausubel et al., eds., *Current Protocols in Molecular Biology,* (John Wiley and Sons, Inc., NY, 1987)], and liposome-mediated transfection [Hawley-Nelson et al., *Focus* 15:73 (1993); Ciccarone et al., *Focus* 15:80, (1993)]. The production of recombinant polypeptides in cultured mammalian cells is disclosed, for example, by Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134. Suitable cultured mammalian cells include the COS-1 (ATCC No. CRL 1650), COS-7 (ATCC No. CRL 1651), BHK (ATCC No. CRL 1632), BHK 570 (ATCC No. CRL 10314), 293 [ATCC No. CRL 1573; Graham et al., *J. Gen. Virol.* 36:59–72 (1977)] and Chinese hamster ovary (e.g. CHO-K1; ATCC No. CCL 61) cell lines. Additional suitable cell lines are known in the art and available from public depositories such as the American Type Culture Collection, Rockville, Md. In general, strong transcription promoters are preferred, such as promoters from SV-40 or cytomegalovirus. See, e.g., U.S. Pat. No. 4,956,288. Other suitable promoters include those from metallothionein genes (U.S. Pat. Nos. 4,579,821 and 4,601,978) and the adenovirus major late promoter.

Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." A preferred selectable marker is a gene encoding resistance to the antibiotic neomycin. Selection is carried out in the presence of a neomycin-type type drug, such as G-418 or the like. Selection systems may also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A referred amplifiable selectable marker is dihydrofolate reductase, which confers resistance to methotrexate. Other drug resistance genes (e.g. hygromycin resistance, multi-drug resistance, puromycin acetyltransferase) can also be used.

Other higher eukaryotic cells can also be used as hosts, including insect cells, plant cells and avian cells. Transformation of insect cells and production of foreign polypeptides therein is disclosed by Guarino et al., U.S. Pat. No. 5,162, 222; Bang et al., U.S. Pat. No. 4,775,624; and WIPO publication WO 94/06463. The use of *Agrobacterium rhizogenes* as a vector for expressing genes in plant cells has been reviewed by Sinkar et al., *J. Biosci.* (Bangalore) 11:47–58, (1987).

Fungal cells, including yeast cells, and particularly cells of the genus Saccharomyces, can also be used within the present invention, such as for producing protein fragments or polypeptide fusions. Methods for transforming yeast cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845, 075. Transformed cells are selected by phenotype determined by the selectable marker, commonly drug resistance or the ability to grow in the absence of a particular nutrient (e.g., leucine). A preferred vector system for use in yeast is the POT1 vector system disclosed by Kawasaki et al., U.S. Pat. No. 4,931,373, which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092) and alcohol dehydrogenase genes. See also U.S. Pat. Nos. 4,990,446; 5,063,154; 5,139,936 and 4,661,454. Transformation systems for other yeasts, including *Hansenula polymorpha, Schizosaccharomyces pombe, Kluyveromyces lactis, Kluyveromyces fragilis, Ustilago maydis, Pichia pastoris, Pichia methanolica, Pichia guillermondii* and *Candida maltosa* are known in the art. See, for example, Gleeson et al., *J. Gen. Microbiol.* 132:3459–3465 (1986) and Cregg, U.S. Pat. No. 4,882,279. Aspergillus cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming Neurospora are disclosed by Lambowitz, U.S. Pat. No. 4,486,533.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell.

Another embodiment of the present invention provides for a peptide or polypeptide comprising an epitope-bearing portion of a Zalpha1 polypeptide of the invention. The epitope of the this polypeptide portion is an immunogenic or antigenic epitope of a polypeptide of the invention. A region of a protein to which an antibody can bind is defined as an "antigenic epitope". See for instance, Geysen, H. M. et al., *Proc. Natl. Acad Sci. USA* 81:3998–4002 (1984).

As to the selection of peptides or polypeptides bearing an antigenic epitope (i.e., that contain a region of a protein molecule to which an antibody can bind), it is well known in the art that relatively short synthetic peptides that mimic part of a protein sequence are routinely capable of eliciting an antiserum that reacts with the partially mimicked protein. See Sutcliffe, J. G. et al. *Science* 219:660–666 (1983). Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals. Peptides that are extremely hydrophobic and those of six or fewer residues generally are ineffective at inducing antibodies that bind to the mimicked protein; longer soluble peptides, especially those containing proline residues, usually are effective.

Antigenic epitope-bearing peptides and polypeptides of the invention are therefore useful to raise antibodies, including monoclonal antibodies, that bind specifically to a polypeptide of the invention. Antigenic epitope-bearing peptides and polypeptides of the present invention contain a sequence of at least nine, preferably between 15 to about 30 amino acids contained within the amino acid sequence of a polypeptide of the invention. However, peptides or polypeptides comprising a larger portion of an amino acid sequence of the invention, containing from 30 to 50 amino acids, or any length up to and including the entire amino acid sequence of a polypeptide of the invention, also are useful for inducing antibodies that react with the protein. Preferably, the amino acid sequence of the epitope-bearing peptide is selected to provide substantial solubility in aqueous solvents (i.e., the sequence includes relatively hydrophilic residues and hydrophobic residues are preferably avoided); and sequences containing proline residues are particularly preferred. All of the polypeptides shown in the sequence listing contain antigenic epitopes to be used according to the present invention, however, specifically designed antigenic epitopes include the peptides defined by SEQ.ID NOs:. The present invention also provides polypeptide fragments or peptides comprising an epitope-bearing portion of a Zalpha1 polypeptide described herein. Such fragments or peptides may comprise an "immunogenic epitope," which is a part of a protein that elicits an antibody response when the entire protein is used as an immunogen. Immunogenic epitope-bearing peptides can be identified using standard methods [see, for example, Geysen et al., supra. See also U.S. Pat. No. 4,708,781 (1987) further describes how to identify a peptide bearing an immunogenic epitope of a desired protein. Specific examples of epitope-bearing polypeptides are those polypeptide which contain SEQ ID NOs: 46–56, especially polypeptides which contain a polypeptide defined by SEQ ID NOs:50–56. SEQ ID NO:50 is a polypeptide comprised of Helices A and B; SEQ ID NO:51 is a polypeptide comprised of helices A, B and C; SEQ ID NO:52 is a polypeptide comprised of helices A, B, C and D; SEQ ID NO:53 is a polypeptide comprised of helices B and C; SEQ ID NO:54 is a polypeptide comprised of helices B, C and D; SEQ ID NO:55 is a polypeptide comprised of helices C and D; and SEQ ID NO:56 is comprised of the polypeptide of SEQ ID NO:2 extending from the beginning of helix C to the end of the polypeptide. Antigenic epitope-bearing peptides and polypeptides of the present invention are useful to raise antibodies that bind with the polypeptides described herein which then can be used to purify the protein in either a native or denatured form or to detect the Zalpha1 polypeptide in a western blot.

Protein Isolation:

Expressed recombinant polypeptides (or chimeric polypeptides) can be purified using fractionation and/or conventional purification methods and media. See, for example, "*Affinity Chromatography: Principles & Methods*" (Pharmacia LKB Biotechnology, Uppsala, Sweden, 1988), *Methods in Enzymol.,* Vol. 182, "Guide to Protein Purification", M. Deutscher, (ed.), pp.529–39 (Acad. Press, San Diego (1990)] and "*Protein Purification, Principles and Practice*" $3^{rd}$ Edition, Scopes, Robert.

Structure of Zalpha1

Zalpha1 is predicted to be a four-helical polypeptide similar to the family of helical cytokines represented by growth hormone, erythropoietin, leptin and interleukin-10. Helix A of Zalpha1 is predicted to include the amino acid residue 23 of SEQ ID NO:2, an asparagine, through amino acid residue 37, an arginine. Helix A is also defined by SEQ ID NO46. Helix B of Zalpha1 is predicted to include amino acid 53 of SEQ ID NO: 2, a phenylalanine, through amino acid residue 67, a phenylalanine. Helix B is also defined by SEQ ID NO:47. Helix C of Zalpha1 is predicted to include amino acid 82 of SEQ ID NO: 2, a phenylalanine, through amino acid residue 96, a leucine residue. Helix C is also defined by SEQ ID NO:48. Helix D of Zalpha1 is predicted to include amino acid 118 of SEQ ID NO: 2, a tyrosine, through amino acid residue 132, an aspartate residue. Helix D is also defined by SEQ ID NO:49.

Uses

By the use of radiation hybrid panels, Zalpha1 was mapped to Xq27.3, in close proximity to FMR1, a gene linked to Fragile-X syndrome. FMR1 is an evolutionarily conserved gene that is transcribed at relatively high levels in brain, testis, heart, lung, kidney and placenta with low to negligible levels in liver, pancreas and skeletal muscle [Hinds et al., *Nature Genet.* 3: 36–43 (1993)]. The function of the FMR1 protein is not known. Studies have shown that FMR1 can bind mRNA and have a nuclear translocation consensus sequence suggesting that it may be a nuclear protein [Ashley et al. *Science* 262: 563–566 (1993); Siomi et al., *Cell* 74: 291–298 (1993)].

The molecular basis for Fragile-X syndrome is due to an unstable, inherited multi-step expansion of a polymorphic triplet repeat sequence (CGG)n within the 5' untranslated region of FMR1. See Hagerman, *Men. Ret. and Devel. Dis. Res. Rev.*1: 276–280 (1995). In a normal population, the number of triplet is polymorphic and ranges from 6–53 units. Carriers of the disease show repeat length of 43–200 units and are termed as having premutations. A full mutation is characterized by expansion of the repeats to greater than 200 units. As a consequence of the expansion, the CGG repeats and the FMR1 promoter sequences become hypermethylated, leading to the inactivation of the transcription of FMR1 and perhaps nearby genes. Premutations are associated with premature ovarian failure, early menopause or precocious puberty in affected individuals. The severity of these and other conditions varies in different individuals and may reflect an underlying dysfunction of the hypothalamic-pituitary-gonadal axis. Nearly all males with a full mutation have mild to severe mental retardation. [Rousseau et al. *Am. J. Hu. Genet.* 55: 225–237 (1994)]. Approximately 50–70% of the females with a fully mutated allele mental impairment [Hagerman et. al. *Pediatrics* 89: 395–400 (1993); Rousseau et al. ibid.]. Full mutation males also exhibit macroorchidism, distinct facies, velvety skins and hyperextensible joints. Female symptoms are more variable which may be due to differential X-inactivation.

While expression of FMR1 is clearly compromised in fragile-X patients with a full mutation, the possibility remains that some of the pleiotropic manifestations of the Fragile-X syndrome may result from the disruption of expression of nearby genes. Methylation is known to inhibit transcription by preventing the direct binding of transcription factors by altering the conformation of DNA. Methylated DNA has been shown to favor Z-DNA formation. As such, hypermethylation of CGG repeats or other mechanisms leading to the extinction of the FMR1 promoter may affect expression of other genes over a considerable distance. Clark et al., *Am. J. Med. Genet.,* 43: 299–396 (1992) have reported that the level of iduronate sulfatase, encoded by the IDS gene (Hunter syndrome), which is located 1000 kb distal to the Fragile-X locus, is decreased in Fragile-X patients.

Zalpha1 has been placed between two fragile sites, FRAXA and FRAXE, in Xq27.3 using a radiation hybrid panel. Due to the close proximity to the FMR1 locus, expression of Zalpha1 may be inhibited by the expansion of the CGG repeats and the ensuing hypermethylation resulting in the extinction of FMR1. The variable phenotypic traits associated with the Fragile-X syndrome may therefore be due at least in part to the absence of Zalpha1 expression. The administration of Zalpha1 polypeptide, its agonists or antagonists may provide a clinical treatment for these conditions The precise physical distance of Zalpha1 to FMR1 can be refined using a number of existing mapping reagents, including somatic cell hybrids, yeast artificial chromosome (YAC) clones, and bacterial artificial chromosome (BAC) clones. The existing somatic cell hybrid mapping panels provide relevant breakpoints at the FRAXA CGG triplet repeat associated with Fragile-X syndrome [Warren et al., *Proc. Nat. Acad. Sci.,* 87: 3856 (1990)], and at the IDS (Hunter syndrome) locus [Suthers et. al. *Am. J. Hum. Genet.,* 47:187 (1990)], distal to FRAXE. The use of these reagents will serve to confirm that the radiation hybrid panel has placed Zalpha1 in the correct chromosomal region with respect to FMR1. A YAC clone is available containing both FRAXA and FRAXE, and which contains BSS H II fragments which are consistent with pulsed-field map of the genome region; therefore it is likely that this YAC does not carry deletions and is thus a valid mapping reagent. A BAC contig connecting FRAXA and FRAXE with one intractable gap is also available for mapping.

Physical mapping of Zalpha1 can easily be accomplished by polymerase chain reaction (PCR), using gene specific primers and the mapping reagents as template. Analysis using the somatic cell hybrid panels will be done initially; confirmation of the regional localization will be followed by higher resolution mapping using the YAC and BAC clones. Mapping of Zalpha1 to one or more BAC clones will provide a precise localization to within 100 kb, and the relative distance to the fragile site can then be easily determined.

Since Zalpha1 transcripts are present in detectable levels in peripheral blood leukocytes, Zalpha1 expression can also be assessed in widely available lymphoblastoid cell lines derived from Fragile-X patients with a range of CGG repeat expansions. Analysis of Zalpha1 transcript levels in these cell lines by Northern blot analysis or by RT/PCR would provide confirmation that Zalpha1 transcription levels are reduced or are absent in Fragile-X patients.

Alteration in Zalph1 transcription in Fragile-X patients can be determined directly by Northern blot analysis or by RT/PCR analysis on pituitary, aortic or other RNA samples isolated from Fragile-X patients. Zalpha1 transcripts of the present invention were found at high levels in the pituitary and in aorta. Lower levels were found in brain, kidney, pancreas, prostate, testis, ovary, thyroid, spinal cord, trachea, adrenal gland. Trace levels were found in placenta, lung, liver, bone marrow and peripheral blood lymphocytes. Expression in the brain and pituitary suggests that Zalpha1 plays a regulatory role in the hypothalamic-pituitary-gonadal axis.

Recent work provides clinical evidence for a connective tissue dysfunction in some Fragile-X patients. Opitz et al., Am. J. Med. Genet. 17: 101–109 (1984) described a connective tissue dysplasia which is characterized by hyperextensible finger joints, flat feet, and mitral valve prolapse. Waldstein and Hagerman, Am. J. Med. Genet., 30: 83–98 (1988) reported on a patient with hypoplasia of the aorta and cardiac valvular abnormalities. Other physical findings commonly seen in Fragile-X patients, such as macroorchidism, prominent ears and hyperelastic skins may also be related to a connective tissue dysplasia. Elastin fibers in these affected tissues were reported to be reduced, abnormal in appearance, fragmented and not orientated. These fibers may fail to provide the appropriate mesh-work for joint stability, skin tensile strength, normal aortic growth and development and proper cardiac valve configuration and function.

It has been suggested that a locus present at or near Xq27.3 is responsible for the structural integrity of elastin or modulation of its production [Waldstein and Hagerman Am. J. Med. Genet. 30: 83–98 (1988)]. Zalpha1 might be that proposed locus. Thus, Zalpha1 polypeptides, agonists or antagonists thereof may be therapeutically useful for the growth, differentiation, maintenance or survival of connective tissues. In particular, that of the cardiovascular and epidermis systems. Clinical indications would include the treatment of blood vessel diseases, macroorchidism, skin disorders, joint instability and other clinical connective tissue dysfunctions. Other applications include cosmetic improvements to normal connective tissues such as enhancement of skin tone and elasticity.

Evaluation of the Zalpha1 polypeptide, fragments thereof, fusion proteins containing Zalpha1, such as Zalpha1-Fc constructs, antibodies, agonists or antagonists for activity in the growth, differentiation, maintenance or survival of connective tissues can be carried out using cell cultures or animal systems. Expression of elastin, collagen, and other phenotypic markers can be used to monitor efficacy in vitro. When administered to murine models, proteins of the present invention are formulated for parental, particularly intravenous or subcutaneous delivery according to standard methods. Delivery to animals would also include the use of viral systems such as the adenovirus, adeno-associated virus and retrovirus systems. Dosing regimen is determined empirically taking into account protein stability and other pharmacokinetic parameters known in the art. The effects of the present invention on growth, differentiation, maintenance or survival of connective and other tissues or organs can be assessed by the examination of histological sections taken from the recipient animals. Particular attention will be paid to tissues or organs in which Zalpha1 is expressed at high levels. Evaluations would include abnormal cell proliferation or cell death. Masson trichrome stain for collagen; orcein and Verhoeff-van Gieson stains for elastin and collagen; and Hale colloidal iron stain for acid mucopolysaccharide. The direct effect of the present invention on skin elasticity and other effects on skin may be assessed by the use of transdermal delivery systems known in the art.

The role of the present invention on the hypothalamic-pituitary-gonadal axis can be assessed by measurements in changes to the circulating levels of gonadotropin, luteinizing hormone, follicle-stimulating hormone and other hormones in the recipient animals.

The present invention also provides reagents with significant therapeutic value. The Zalpha1 polypeptide (naturally occurring or recombinant), fragments thereof, antibodies and anti-idiotypic antibodies thereto, along with compounds identified as having binding affinity to the Zalpha1 polypeptide, should be useful in the treatment of conditions associated with abnormal physiology or development, including abnormal proliferation, e.g., cancerous conditions, or degenerative conditions. For example, a disease or disorder associated with abnormal expression or abnormal signaling by a Zalpha1 polypeptide should be a likely target for an agonist or antagonist of the Zalpha1 polypeptide.

Antibodies to the Zalpha1 polypeptide can be purified and then administered to a patient. These reagents can be combined for therapeutic use with additional active or inert ingredients, e.g., in pharmaceutically acceptable carriers or diluents along with physiologically innocuous stabilizers and excipients. These combinations can be sterile filtered and placed into dosage forms as by lyophilization in dosage vials or storage in stabilized aqueous preparations. This invention also contemplates use of antibodies, binding fragments thereof or single-chain antibodies of the antibodies including forms which are not complement binding.

The quantities of reagents necessary for effective therapy will depend upon many different factors, including means of administration, target site, physiological state of the patient, and other medications administered. Thus, treatment dosages should be titrated to optimize safety and efficacy. Typically, dosages used in vitro may provide useful guidance in the amounts useful for in vivo administration of these reagents. Animal testing of effective doses for treatment of particular disorders will provide further predictive indication of human dosage. Methods for administration include oral, intravenous, peritoneal, intramuscular, or transdermal administration. Pharmaceutically acceptable carriers will include water, saline, buffers to name just a few. Dosage ranges would ordinarily be expected from 1 $\mu$g to 1000 $\mu$g per kilogram of body weight per day. However, the doses by be higher or lower as can be determined by a medical doctor with ordinary skill in the art. For a complete discussion of drug formulations and dosage ranges see Remington's Pharmaceutical Sciences, $18^{th}$ Ed., (Mack Publishing Co., Easton, Pa., 1996), and Goodman and Gilman's: *The Pharmacological Bases of Therapeutics*, $9^{th}$ Ed. (Pergamon Press 1996).

Introduction of Nucleic Acids into Mammalian Cells

If a mammal has a mutated or lacks a Zalpha1 gene, the Zalpha1 gene can be introduced into the cells of the mammal. In one embodiment, a gene encoding a Zalpha1 polypeptide is introduced in vivo in a viral vector. Such vectors include an attenuated or defective DNA virus, such as but not limited to herpes simplex virus (HSV), papillomavirus, Epstein Barr virus (EBV), adenovirus, adeno-associated virus (AAV), and the like. Defective viruses, which entirely or almost entirely lack viral genes, are preferred. A defective virus is not infective after introduction into a cell. Use of defective viral vectors allows for administration to cells in a specific, localized area, without concern that the vector can infect other cells. Examples of particular vectors include, but are not limited to, a defective herpes virus 1 (HSV1) vector [Kaplitt et al., *Molec. Cell. Neurosci.*, 2:320–330 (1991)], an attenuated adenovirus vector, such as the vector described by Stratford-Perricaudet et al., *J. Clin. Invest.*, 90:626–630 (1992), and a defective adeno-associated virus vector [Samulski et al., *J. Virol.*, 61:3096–3101 (1987); Samulski et al. *J. Virol.*, 63:3822–3828 (1989)].

In another embodiment, the gene can be introduced in a retroviral vector, e.g., as described in Anderson et al., U.S. Pat. No. 5,399,346; Mann et al., *Cell*, 33:153 (1983); Temin et al., U.S. Pat. No. 4,650,764; Temin et al., U.S. Pat. No. 4,980,289; Markowitz et al., *J. Virol.*, 62:1120 (1988); Temin et al., U.S. Pat. No. 5,124,263; International Patent Publication No. WO 95/07358; and *Blood*, 82:845 (1993).

Alternatively, the vector can be introduced by lipofection in vivo using liposomes. Synthetic cationic lipids can be used to prepare liposomes for in vivo transfection of a gene encoding a marker [Felgner et al., *Proc. Natl. Acad. Sci. USA*, 84:7413–7417 (1987); see Mackey et al., *Proc. Natl. Acad. Sci. USA*, 85:8027–8031 (1988)]. The use of lipofection to introduce exogenous genes into specific organs in vivo has certain practical advantages. Molecular targeting of liposomes to specific cells represents one area of benefit. It is clear that directing transfection to particular cells represents one area of benefit. It is clear that directing transfection to particular cell types would be particularly advantageous in a tissue with cellular heterogeneity, such as the pancreas, liver, kidney, and brain. Lipids may be chemically coupled to other molecules for the purpose of targeting. Targeted peptides, e.g., hormones or neurotransmitters, and proteins such as antibodies, or non-peptide molecules could be coupled to liposomes chemically.

It is possible to remove the cells from the body and introduce the vector as a naked DNA plasmid and then re-implant the transformed cells into the body. Naked DNA vector for gene therapy can be introduced into the desired host cells by methods known in the art, e.g., transfection, electroporation, microinjection, transduction, cell fusion, DEAE dextran, calcium phosphate precipitation, use of a gene gun or use of a DNA vector transporter [see, e.g., Wu et al., *J. Biol. Chem.*, 267:963–967 (1992); Wu et al., *J. Biol. Chem.*, 263:14621–14624 (1988)].

Zalpha1 polypeptides can also be used to prepare antibodies that specifically bind to Zalpha1 polypeptides. These antibodies can then be used to manufacture anti-idiotypic antibodies. As used herein, the term "antibodies" includes polyclonal antibodies, monoclonal antibodies, antigen-binding fragments thereof such as F(ab')$_2$ and Fab fragments, and the like, including genetically engineered antibodies.

Methods for preparing polyclonal and monoclonal antibodies are well known in the art (see for example, Sambrook et al., *Molecular Cloning: A Laboratory Manual*, Second Edition, (Cold Spring Harbor, N.Y., 1989); and Hurrell, J. G. R., Ed., *Monoclonal Hybridoma Antibodies: Techniques and Applications* (CRC Press, Inc., Boca Raton, Fla., 1982). As would be evident to one of ordinary skill in the art, polyclonal antibodies can be generated from a variety of warm-blooded animals such as horses, cows, goats, sheep, dogs, chickens, rabbits, mice, and rats. The immunogenicity of a Zalpha1 polypeptide may be increased through the use of an adjuvant such as Freund's complete or incomplete adjuvant. A variety of assays known to those skilled in the art can be utilized to detect antibodies which specifically bind to Zalpha1 polypeptides. Exemplary assays are described in detail in *Antibodies: A Laboratory Manual*, Harlow and Lane (Eds.), (Cold Spring Harbor Laboratory Press, 1988). Representative examples of such assays include: concurrent immunoelectrophoresis, radio-immunoassays, radio-immunoprecipitations, enzyme-linked immunosorbent assays (ELISA), dot blot assays, inhibition or competition assays, and sandwich assays.

Antibodies are determined to be specifically binding if: 1) they exhibit a threshold level of binding activity, and 2) they do not cross-react with prior art polypeptide molecules. First, antibodies herein specifically bind if they bind to a Zalpha1 polypeptide, peptide or epitope with a binding affinity ($K_a$) of $10^6$ $M^{-1}$ or greater, preferably $10^7$ $M^{-1}$ or greater, more preferably $10^8$ $M^{-1}$ or greater, and most preferably $10^9$ $M^{-1}$ or greater. The binding affinity of an antibody can be readily determined by one of ordinary skill in the art, for example, by Scatchard analysis.

Second, antibodies are determined to specifically bind if they do not cross-react with polypeptides of the prior art. Antibodies do not significantly cross-react with related polypeptide molecules, for example, if they detect Zalpha1 but not known related polypeptides using a standard Western blot analysis (Ausubel et al., ibid.). Examples of known related polypeptides are orthologs, proteins from the same species that are members of a protein family (e.g. IL-16), Zalpha1 polypeptides, and non-human Zalpha1. Moreover, antibodies may be "screened against" known related polypeptides to isolate a population that specifically binds to the inventive polypeptides. For example, antibodies raised to Zalpha1 are adsorbed to related polypeptides adhered to insoluble matrix; antibodies specific to Zalpha1 will flow through the matrix under the proper buffer conditions. Such screening allows isolation of polyclonal and monoclonal antibodies non-crossreactive to closely related polypeptides, *Antibodies: A Laboratory Manual*, Harlow and Lane (eds.) (Cold Spring Harbor Laboratory Press, 1988); *Current Protocols in Immunology*, Cooligan, et al. (eds.), National Institutes of Health (John Wiley and Sons, Inc., 1995). Screening and isolation of specific antibodies is well known in the art. See, *Fundamental Immunology*, Paul (eds.) (Raven Press, 1993); Getzoff et al., *Adv. in Immunol.* 43: 1–98 (1988); *Monoclonal Antibodies: Principles and Practice*, Goding, J. W. (eds.), (Academic Press Ltd., 1996); Benjamin et al., *Ann. Rev. Immunol.* 2: 67–101 (1984).

A variety of assays known to those skilled in the art can be utilized to detect antibodies which specifically bind to Zalpha1 proteins or peptides. Exemplary assays are described in detail in *Antibodies: A Laboratory Manual*, Harlow and Lane (Eds.) (Cold Spring Harbor Laboratory Press, 1988). Representative examples of such assays include: concurrent immunoelectrophoresis, radioimmunoassay, radioimmuno-precipitation, enzyme-linked immunosorbent assay (ELISA), dot blot or Western blot assay, inhibition or competition assay, and sandwich assay. In addition, antibodies can be screened for binding to wild-type versus mutant Zalpha1 protein or polypeptide.

Antibodies to Zalpha1 may be used for tagging cells that express the protein, for affinity purification, within diagnostic assays for determining circulating levels of soluble protein polypeptides, and as antagonists to block ligand binding and signal transduction in vitro and in vivo. Anti-idiotypic antibodies can be used to discover a receptor of Zalpha1.

Radiation hybrid mapping is a somatic cell genetic technique developed for constructing high-resolution, contiguous maps of mammalian chromosomes [Cox et al., *Science* 250:245–250 (1990)]. Partial or full knowledge of a gene's sequence allows the designing of PCR primers suitable for use with chromosomal radiation hybrid mapping panels. Commercially available radiation hybrid mapping panels which cover the entire human genome, such as the Stanford G3 RH Panel and the GeneBridge 4 RH Panel (Research Genetics, Inc., Huntsville, Ala.), are available. These panels enable rapid, PCR based, chromosomal localizations and ordering of genes, sequence-tagged sites (STSs), and other nonpolymorphic- and polymorphic markers within a region of interest. This includes establishing directly proportional physical distances between newly discovered genes of interest and previously mapped markers. The precise knowledge of a gene's position can be useful in a number of ways including: 1) determining if a sequence is part of an existing contig and obtaining additional surrounding genetic sequences in various forms such as YAC-, BAC- or cDNA clones, 2) providing a possible candidate gene for an inheritable disease which shows linkage to the same chromosomal region, and 3) for cross-referencing model organisms such as mouse which may be beneficial in helping to determine what function a particular gene might have.

The present invention also provides reagents which will find use in diagnostic applications. For example, the Zalpha1 gene has been mapped on chromosome Xq27.3. A Zalpha1 nucleic acid probe could to used to check for abnormalities on the X chromosome. For example, a probe comprising Zalpha1 DNA or RNA or a subsequence thereof can be used to determine if the Zalpha1 gene is present on chromosome Xq27.3 or if a mutation has occurred. Detectable chromosomal aberrations at the Zalpha1 gene locus include but are not limited to aneuploidy, gene copy number changes, insertions, deletions, restriction site changes and rearrangements. Such aberrations can be detected using polynucleotides of the present invention by employing molecular genetic techniques, such as restriction fragment length polymorphism (RFLP) analysis, short tandem repeat (STR) analysis employing PCR techniques, and other genetic linkage analysis techniques known in the art [Sambrook et al., ibid.; Ausubel, et. al., ibid.; Marian, A. J., *Chest*, 108: 255–265, (1995)].

The invention is further illustrated by the following non-limiting examples.

EXAMPLE 1

Production of a Pituitary Gland cDNA Library

RNA extracted from cells of pituitary gland was purchased from Clontech, Palo Alto, Calif. and reversed transcribed in the following manner. The first strand cDNA reaction contained 10 µl of human pituitary twice poly d(T)-selected poly (A)+ mRNA (Clontech, Palo Alto, Calif.) at a concentration of 1.0 mg/ml, and 2 µl of 20 pmole/µl first strand primer ZC6191 SEQ ID NO: 4 (GTC TGG GTT CGC TAC TCG AGG CGG CCG CTA TTT TTT TTT TTT TTT TTT) containing an Xho I restriction site. The mixture was heated at 70° C. for 2.0 minutes and cooled by chilling on ice. First strand cDNA synthesis was initiated by the addition of 8 µl of first strand buffer (5×SUPERSCRIPT™ buffer; Life Technologies, Gaithersburg, Md.), 4 µl of 100 mM dithiothreitol, and 2 µl of a deoxynucleotide triphosphate (dNTP) solution containing 10 mM each of dTTP, dATP, dGTP and 5-methyl-dCTP (Pharmacia LKB Biotechnology, Piscataway, N.J.) to the RNA-primer mixture. The reaction mixture was incubated at 37° C. for 2 minutes, followed by the addition of 10 µl of 200 U/µl RNase H⁻ reverse transcriptase (SUPERSCRIPT II®; Life Technologies). The efficiency of the first strand synthesis was analyzed in a parallel reaction by the addition of 10 µCi of $^{32}$P-αdCTP to a 5 µl aliquot from one of the reaction mixtures to label the reaction for analysis. The reactions were incubated at 37° C. for 5 minutes, 45° C. for 45 minutes, then incubated at 50° C. for 10 minutes. Unincorporated $^{32}$P-αdCTP in the labeled reaction was removed by chromatography on a 400 pore size gel filtration column (Clontech Laboratories). The unincorporated nucleotides and primers in the unlabeled first strand reactions were removed by chromatography on 400 pore size gel filtration column (Clontech Laboratories). The length of labeled first strand cDNA was determined by agarose gel electrophoresis.

The second strand reaction contained 100 µl of the unlabeled first strand cDNA, 30 µl of 5×polymerase I buffer (125 mM Tris: HCl, pH 7.5, 500 mM KCl, 25 mM MgCl$_2$, 50 mM (NH$_4$)$_2$SO$_4$)), 2.0 µl of 100 mM dithiothreitol, 3.0 µl of a solution containing 10 mM of each deoxynucleotide triphosphate, 7 µl of 5 mM β-NAD, 2.0 µl of 10 U/µl *E. coli* DNA ligase (New England Biolabs; Beverly, Mass.), 5 µl of 10 U/µl *E. coli* DNA polymerase I (New England Biolabs), and 1.0 µl of 2 U/µl RNase H (Life Technologies). A 10 µl aliquot from one of the second strand synthesis reactions was labeled by the addition of 10 µCi $^{32}$P-αdCTP to monitor the efficiency of second strand synthesis. The reactions were incubated at 16° C. for two hours, followed by the addition of 1 µl of a 10 mM dNTP solution and 5.0 µl T4 DNA polymerase (10 U/µl, Boehringer Mannheim, Indianapolis, Ind.) and incubated for an additional 10 minutes at 16° C. Unincorporated $^{32}$P-αdCTP in the labeled reaction was removed by chromatography through a 400 pore size gel filtration column (Clontech Laboratories) before analysis by agarose gel electrophoresis. The reaction was terminated by the addition of 10.0 µl 0.5 M EDTA and extraction with phenol/chloroform and chloroform followed by ethanol precipitation in the presence of 3.0 M Na acetate and 2 µl of Pellet Paint carrier (Novagen, Madison, Wis.). The yield of cDNA was estimated to be approximately 2 µg from starting mRNA template of 10 µg.

Eco RI adapters were ligated onto the 5' ends of the cDNA described above to enable cloning into an expression vector. A 12.5 µl aliquot of cDNA (~2.0 µg) and 3 µl of 69 pmole/µl of Eco RI adapter (Pharmacia LKB Biotechnology Inc.) were mixed with 2.5 µl 10×ligase buffer (660 mM Tris-HCl pH 7.5, 100 mM MgCl$_2$), 2.5 µl of 10 mM ATP, 3.5 µl 0.1 M DTT and 1 µl of 15 U/µl T4 DNA ligase (Promega Corp., Madison, Wis.). The reaction was incubated 1 hour at 5° C., 2 hours at 7.5° C., 2 hours at 10° C., 2 hours at 12.5° C. and 16 hours at 10° C. The reaction was terminated by the addition of 65 µl H$_2$O and 10 µl 10×H buffer (Boehringer Mannheim) and incubation at 70° C. for 20 minutes.

To facilitate the directional cloning of the cDNA into an expression vector, the cDNA was digested with Xho I, resulting in a cDNA having a 5' Eco RI cohesive end and a 3' Xho I cohesive end. The Xho I restriction site at the 3' end of the cDNA had been previously introduced. Restriction enzyme digestion was carried out in a reaction mixture by the addition of 1.0 μl of 40 U/μl Xho I (Boehringer Mannheim). Digestion was carried out at 37° C. for 45 minutes. The reaction was terminated by incubation at 70° C. for 20 minutes and chromatography through a 400 pore size gel filtration column (Clontech Laboratories).

The cDNA was ethanol precipitated, washed with 70% ethanol, air dried and resuspended in 13.5 μl water, 2 μl of 10×kinase buffer (660 mM Tris-HCl, pH 7.5, 100 mM $MgCl_2$), 0.5 μl 0.1 M DTT, 2 μl 10 mM ATP, 2 μl T4 polynucleotide kinase (10 U/μl, Life Technologies). Following incubation at 37° C. for 30 minutes, the cDNA was ethanol precipitated in the presence of 2.5 M Ammonium Acetate, and electrophoresed on a 0.8% low melt agarose gel. The contaminating adapters and cDNA below 0.6 Kb in length were excised from the gel. The electrodes were reversed, and the cDNA was electrophoresed until concentrated near the lane origin. The area of the gel containing the concentrated cDNA was excised and placed in a microfuge tube, and the approximate volume of the gel slice was determined. An aliquot of water approximately three times the volume of the gel slice (300 μl) and 35 μl 10×β-agarose I buffer (New England Biolabs) was added to the tube, and the agarose was melted by heating to 65° C. for 15 minutes. Following equilibration of the sample to 45° C., 3 μl of 1 U/μl β-agarose I (New England Biolabs) was added, and the mixture was incubated for 60 minutes at 45° C. to digest the agarose. After incubation, 40 μl of 3 M Na acetate was added to the sample, and the mixture was incubated on ice for 15 minutes. The sample was centrifuged at 14,000×g for 15 minutes at room temperature to remove undigested agarose. The cDNA was ethanol precipitated, washed in 70% ethanol, air-dried and resuspended in 20 μl water.

Following recovery from low-melt agarose gel, the cDNA was cloned into the Eco RI and Xho I sites of pBLUE-SCRIPT SK+ vector (Gibco/BRL) and electroporated into DH10B cells. Bacterial colonies containing ESTs of known genes were identified and eliminated from sequence analysis by reiterative cycles of probe hybridization to hi-density colony filter arrays (Genome Systems). cDNAs of known genes were pooled in groups of 50–100 inserts and were labeled with $^{32}P$ using a MEGAPRIME labeling kit (Amersham). Colonies which did not hybridize to the probe mixture were selected for sequencing. Sequencing was done using an ABI 377 sequencer using either the T3 or the reverse primer. The resulting data were analyzed which resulted in the identification of the novel EST LPIF1021273 (SEQ ID NO: 3).

EXAMPLE 2

Discovery of the Zalpha1 Gene

The cDNA clone which corresponded to the EST of SEQ ID NO: 3 was sequenced which resulted in the Zalpha1 DNA sequence and Zalpha1 amino acid sequence of SEQ ID NO: 1 and SEQ ID NO: 2 respectively.

EXAMPLE 3

Northern Blot Analysis

Human multiple tissue blots1, 2, 3, and a human RNA dot blot (Clontech) were probed to determine the tissue distribution of Zalpha1. A 1.2 kb PCR product representing the Zalpha1 cDNA was generated using primers (SEQ ID NO:26) and (SEQ ID NO:27), made to the pBLUESCRIPT SK+®, T7 promoter and M13 reverse primer sequence, respectively. The resulting fragment was electrophoresed on a 0.7% agarose gel. The DNA was extracted from the gel slab with a QIAquick Gel Extraction Kit (Qiagen). 100 ng of this DNA was labeled with $P^{32}$ using the REIPRIME® Labeling System (Amersham) and unincorporated radioactivity was removed with a NucTrap Probe Purification Column (Stratagene). Multiple tissue northerns and a human RNA master blot were prehybridized 3 hours with 10 ml EXPRESSHYB® Solution (Clontech) containing 1 mg salmon sperm DNA which was boiled 5 minutes and then iced 1 minute and added to 10 ml of ExpressHyb Solution, mixed and added to blots. Hybridization was carried out overnight at 65° C. Initial wash conditions were as follows: 2×SSC, 0.05% SDS RT for 40 minutes with several changes of solution then 0.1×SSC, 0.1% SDS at 50° C. for 40 minutes, 1 solution change. Blots were than exposed to film a −80° C. for 2.5 hours.

The RNA dot blot showed high expression of Zalpha1 in pituitary and aorta. The multiple tissue northern blots showed abundant expression in thyroid, spinal cord, brain, kidney and pancreas with lower expression in heart, spleen, prostate, testis, stomach, trachea and adrenal gland.

EXAMPLE 4

Chromosomal Assignment and Placement of Zalpha1

Zalpha1 was mapped to the X chromosome using the commercially available "GeneBridge 4 Radiation Hybrid Panel" (Research Genetics, Inc., Huntsville, Ala.). The GeneBridge 4 Radiation Hybrid Panel contains PCRable DNAs from each of 93 radiation hybrid clones, plus two control DNAs (the HFL donor and the A23 recipient). A publicly available WWW server (http://www-genome.wi.mit.edu/cgi-bin/contig/rhmapper.p1) allows mapping relative to the Whitehead Institute/MIT Center for Genome Research's radiation hybrid map of the human genome (the "WICGR" radiation hybrid map) which was constructed with the GeneBridge 4 Radiation Hybrid Panel.

For the mapping of Zalpha1 with the "GeneBridge 4 RH Panel", 20 μl reactions were set up in a PCRable 96-well microtiter plate (Stratagene, La Jolla, Calif.) and used in a "RoboCycler Gradient 96" thermal cycler (Stratagene). Each of the 95 PCR reactions consisted of 2 μl 10×KlenTaq PCR reaction buffer (CLONTECH Laboratories, Inc., Palo Alto, Calif.), 1.6 μl dNTPs mix (2.5 mM each, PERKIN-ELMER, Foster City, Calif.), 1 μl sense primer, (SEQ ID NO: 5) 15,869, 5' GCA GCA GTC CCA CAG ATG 3', 1 μl antisense primer, (SEQ ID NO: 6) ZC 15,868, 5' TGG GCT GAG TGC TTG TTT 3', 2 μl "RediLoad" (Research Genetics, Inc., Huntsville, Ala.), 0.4 μl 50×Advantage Klen-Taq Polymerase Mix (Clontech Laboratories, Inc.), 25 ng of DNA from an individual hybrid clone or control and x μl $ddH_2O$ for a total volume of 20 μl. The reactions were overlaid with an equal amount of mineral oil and sealed. The PCR cycler conditions were as follows: an initial 1 cycle 5 minute denaturation at 95° C., 35 cycles of a 1 minute denaturation at 95° C., 1 minute annealing at 64° C. and 1.5 minute extension at 72° C., followed by a final 1 cycle extension of 7 minutes at 72° C. The reactions were separated by electrophoresis on a 2% agarose gel (Life Technologies, Gaithersburg, Md.).

The results showed that Zalpha1 maps 4.71 cR__3000 from the framework marker WI-5285 on the WICGR radiation hybrid map. The use of surrounding markers positions Zalpha1 in the Xq27.3 region on the integrated LDB map of the X chromosome (The Genetic Location Database, University of Southhampton, WWW server: http://cedar.genetics.soton.ac.uk/public_html/).

EXAMPLE 5

Construction of Untagged, Amino Terminal Glu-Glu Tagged, and Carboxy Terminal Glu-Glu Tagged Mammalian Expression Vectors for Zalpha1

Three mammalian vectors which express Zalpha1 are being constructed using a yeast recombination vector. Three different variations of the Zalpha1 polypeptide were generated; (i) untagged, (ii) amino terminal Glu-Glu tagged, and (iii) carboxy terminal Glu-Glu tagged. The amino acid sequence of the Glu-Glu tag is Glu-Glu-Tyr-Met-Pro-Met-Glu (SEQ ID NO:25)

The vectors can be made as follows.

Generation of Recombination Linkers

The construction of the expression vector in which there is no Glu-Glu tag attached to the Zalpha1 can be done as follows. Both a 5' and 3' linkers can be constructed which do not encode a Glu-Glu tag and which ligate by means of homologous recombination with the digested plasmid and with the Zalpha1 gene so as to produce a plasmid containing the Zalpha1 gene. This is done by transfecting the two linker DNAs, Zalpha1 gene and the digested plasmid simultaneously into yeast. The plasmid number can be amplified in the yeast, isolated from the yeast, transfected to *E. coli*, amplified, isolated and then transfected into mammalian cells to produce Zalpha1. The amino acid carboxy terminal tagged versions are generated in the same manner except that the appropriately tagged recombination linkers are used. The yeast plasmid pCZR199 was engineered from vector pRS316, [Sikorski and Hieter, *Genetics* 122: 19–27 (1989) into which a two PVuII sites were engineered and a EcoRI, Xbz were engineered between the two PVUII sites.

A.) Generation of the Untagged Amino Terminus

The DNA linker which homologously recombines with the 3' end of the digested plasmid and the 5' end of the Zalph1 gene and does not add a Glu-Glu tag to Zalpha1 can be made as follows.

A solution containing 4 pmole each of the sense oligonucleotide ZC16,469 5' TCG CCC AGC CAG GAA ATC CAT GCC GAG TTC CAA CGC GGC CGT AGA 3' (SEQ ID NO:8) and the antisense oligonucleotide ZC16,465, 5' CAG CAG CCG CAG CTG TTC CAT GAG CTG GCT GTT CTC GAT TCT ACG GCC GCG TTG GAA CTC GG3' (SEQ ID NO:9) are amplified together by PCR. The amplified product of these two oligonucleotides was further extended in the same reaction tube, in the same PCR reaction using 400 picomoles of the sense primer ZC16,470 5' CTG CTG TGT GGC GCC GTC TTC GTT TCG CCC AGC CAG GAA ATC CAT 3' (SEQ ID NO:7) and 400 picomoles of the antisense primer ZC16,028 5' TAC CTG GCG CAG CAG GCT GGC CCT CTC GCA CAC CAG CAG CCG CAG CTG TTC CAT 3' (SEQ ID NO:10).

The PCR mixture for the reaction contained 40 µl of 10×PCR buffer,8 µl EXTAG (both from Takara), 8 µl of 2.5 mM nucleotide triphosphate mix Takara) and 300 µl of water. The PCR reaction was incubated at 94° C. for 1.5 minutes, and then run for 10 cycles each individual cycle being comprised of 30 seconds at 94° C., 1 minute at 50° C. and 1 minutes at 72° C. The reaction was ended with an incubation for 10 minutes at 72° C.

This resulted in the recombination linker

5' CTG CTG TGT GGC GCC GTC TTC GTT TCG CCC AGC CAG GAA ATC CAT GCC GAG TTC CAA CGC GGC CGT AGA ATC GAG AAC AGC CAG CTC ATG GAA CAG CTG CGG CTG CTG GTG TGC GAG AGG GCC AGC CTG CTG CGC CAG GTA 3' (SEQ ID NO:11).

B) Untagged Carboxy Terminus

The DNA linker which homologously recombines with the 5' end of the digested plasmid and the 3' end of the Zalph1 gene and does not add a Glu-Glu tag to the carboxy terminus of Zalpha1 can be made as follows.

4 picomoles of the sense oligonucleotide ZC,16,484, 5' GAC GAA GAC GAC GAC GAC GAA GAA GAG GAG GAT GAT TAT TAA TCT AGA GGA TCT GGG GTG GCA TCC CTG T 3' (SEQ ID NO:13) and 4 picomoles of the antisense oligonucleotide ZC14,455 5' CAG GAG AGG CAC TGG GGA GGG GTC ACA GGG ATG CCA CCC CAG ATC C 3' (SEQ ID NO:14) were added together in a PCR reaction mixture. Also added to the mixture are 400 picomoles of sense primer ZC16,027 5' GAT GAG ATG AAA CAG TGC TTT GGC TGG GAT GAC GAC GAA GAC GAC GAC GAC GAA 3' (SEQ ID NO:12)and 400 picomoles of the antisense primer ZC14,394 5' GGC ACT GGA GTG GCA ACT TCC AGG GCC AGG AGA GGC ACT GGG GAG G 3' (SEQ ID NO:15) The PCR mixture for the reaction further contained 40 µl of 10×PCR buffer,8 µl EXTAG (both from Takara), 8 µl of 2.5 mM nucleotide triphosphate mix Takara) and 300 µl of water. The PCR reaction was incubated at 94° C. for 1.5 minutes, and then run for 10 cycles each individual cycle being comprised of 30 seconds at 94° C., 1 minute at 50° C. and 1 minutes at 72° C. The reaction was ended with an incubation for 10 minutes at 72°.

This produced the following oligonucleotide linker which homologously recombines to the 5' end of the digested plasmid and the 3' end of the Zalpha1 gene:

5' GAT GAG ATG AAA CAG TGC TTT GGC TGG GAT GAC GAC GAA GAC GAC GAC GAC GAA GAA GAG GAG GAT GAT TAT TAA TCTAGAGGAT CTGGGGTGGC ATCCCTGTGA CCCCTCCCCA GTGCCTCTCC TGGCCCTGGA AGTTGCCACT CCAGTGCC 3' (SEQ ID NO:16).

C) Glu-Glu Tagged Amino Terminus

A linker which would homologously recombine with the 3' end of the digested plasmid and the 5' end of the Zalpha1 gene and which when the Zalpha1 gene was expressed would attach a Glu-Glu tag onto the amino terminus of Zalpha1 was produced as follows. 4 picomoles of the sense oligonucleotide ZC14,397 5' CCG AGT TCC AAC GCG GCC GTA GAG AGG AGT ATA TGC CTA TGG AG 3' (SEQ ID NO:18) and 4 picomoles of the antisense oligonucleotide ZC15,485 5' CAG CAG CCG CAG CTG TTC CAT GAG CTG GCT GTT CTC GAT CTC CAT AGG CAT ATA CTC CTC TCT ACG 3' (SEQ ID NO:19) were added together in a PCR reaction mixture. Also added to the mixture were 400 picomoles of the sense primer ZC14,396 5' GTT TCG CCC AGC CAG GAA ATC CAT GCC GAG TTC CAA CGC GGC CGT 3' (SEQ ID NO:17) and 400 picomoles of the antisense primer ZC16,028 5' TAC CTG GCG CAG CAG GCT GGC CCT CTC GCA CAC CAG CAG CCG CAG CTG TTC CAT 3' (SEQ ID NO:10) The PCR mixture for the reaction further contained 40 µl of 10×PCR buffer,8 µl EXTAG (both from Takara), 8 µl of 2.5 mM nucleotide triphosphate mix Takara) and 300 µl of water. The PCR reaction was incubated at 94° C. for 1.5 minutes, and then run for 10 cycles each individual cycle being comprised of 30 seconds at 94° C., 1 minute at 50° C. and 1 minutes at 72° C. The reaction was ended with an incubation for 10 minutes at 72°.

This produced the following linker:

5' GTT TCG CCC AGC CAG GAA ATC CAT GCC GAG TTC CAA CGC GGC CGT AGA GAG GAG TAT ATG CCT ATG GAG ATC GAG AAC AGC CAG CTC ATG GAA CAG CTG CGG CTG CTG GTG TGC GAG AGG GCC AGC CTG CTG CGC CAG GTA 3' (SEQ ID NO:20).

D) Glu-Glu Tagged Carboxy Terminus

A linker which would homologously recombine with the 5' end of the digested plasmid and the 3' end of the Zalpha1 gene and which when the Zalpha1 gene was expressed would attach a Glu-Glu tag onto the carboxy terminus of Zalpha1 was produced as follows. 4 picomoles of the sense oligonucleotide ZC16,486, 5' GAC GAA GAC GAC GAC GAC GAA GAA GAG GAG GAT GAT TAT GAA GAA TAC ATG CCC ATG GAA TAA 3' (SEQ ID NO:21) and 4 picomoles of the antisense oligonucleotide ZC14,393 5' AT GCCACCCCAG ATCCTCTAGA TTA TTC CAT GGG CAT GTA TTC TTC 3' (SEQ ID NO:22) were added together in a PCR reaction mixture. Also added to the reaction mixture were 400 picomoles of the sense primer ZC16,027, 5' GAT GAG ATG AAA CAG TGC TTT GGC TGG GAT GAC GAC GAA GAC GAC GAC GAC GAA 3' (SEQ ID NO:12) and 400 picomoles of the antisense primer ZC14,395

5' GGCAC TGGGGAGGGG TCACAGGGAT GCCAC-CCCAG ATCCTCTAGA 3' (SEQ ID NO:23). The PCR mixture for the reaction further contained 40 µl of 10×PCR buffer,8 µl EXTAG (both from Takara), 8 µl of 2.5 mM nucleotide triphosphate mix Takara) and 300 µl of water. The PCR reaction was incubated at 94° C. for 1.5 minutes, and then run for 10 cycles each individual cycle being comprised of 30 seconds at 94° C., 1 minutes at 50° C. and 1 minutes at 72° C. The reaction was ended with an incubation for 10 minutes at 72°.

This produced the following oligonucleotide linker:

5' GAT GAG ATG AAA CAG TGC TTT GGC TGG GAT GAC GAC GAA GAC GAC GAC GAC GAA GAA GAG GAG GAT GAT TAT GAA GAA TAC ATG CCC ATG GAA TAA TCTAGAGGAT CTGGGGTGGC ATCCCT-GTGA CCCCTCCCCA GTGCC 3' (SEQ ID NO:24)

Plasmid Assembly in Yeast

Following the procedure for plasmid assembly through recombination of homologous DNA sequences in yeast, the following three versions of zalpha1 are generated.

A) Untagged Version of Zalpha1

A mixture of 0.1 µg linear pCZR199, 1 mg full length Zalpha1 cDNA, and about 1 μg of each of the untagged amino terminus and untagged carboxy terminus recombination linkers are mixed in a total volume of 10 ml. This mixture is used to transform competent yeast cells (*Saccharomyces cerevisiae*). Plasmid DNA from the successful transformations are transferred to *E. coli* and the desired constructs were identified by DNA sequence analysis. The plasmids can then be transfected into mammalian cells such as Chinese Hamster Ovary (CHO) cells.

B) Amino Terminal Glu-Glu Tagged Version of Zalpha1

Same as above except the Glu-Glu tagged amino terminus and untagged carboxy terminus recombination linkers were used.

C) Carboxy Terminal Glu-Glu Tagged Version of Zalpha1

Same as above except the Glu-Glu tagged carboxy terminus and untagged amino terminus recombination linkers were used.

EXAMPLE 6

Expression of Zalpha1 in *Pichia Methanolica*

Homologous Recombination/Zalpha1

Expression of Zalpha1 in *Pichia methanolica* utilizes the expression system described in co-assigned PCT WO. 97/17450. An expression plasmid containing all or part of a polynucleotide encoding Zalpha1 is constructed via homologous recombination. The expression vector is built from pCZR204, which contains the AUG1 promoter, followed by the αFpp leader sequence, followed by an amino-terminal peptide tag, a blunt-ended SmaI restriction site, a carboxy-terminal peptide tag, a translational STOP codon, followed by the AUG1 terminator, the ADE2 selectable marker, and finally the AUG1 3' untranslated region. Also included in this vector are the URA3 and CEN-ARS sequences required for selection and replication in *S. cerevisiae,* and the $Amp^R$ and colE1 ori sequences required for selection and replication in *E. coli.* The Zalpha1 sequence inserted into this vector begins at residue 27 (Ala) of the Zalpha1 amino acid sequence.

In the present case three expression plasmids were produced for expression of Zalpha1 in *P. methanolica.* The plasmids are: one called the NEE-zalpha1 construct produced a Zalpha1 polypeptide in which the N-terminus was tagged with a Glu-Glu tag (SEQ ID NO:25), one called the CEE-zalpha1 construct produced a Zalpha1 polypeptide in which the C-terminus was tagged with a Glu-Glu tag (SEQ ID NO:25) and one in which the Zalpha1 was untagged. In each case two linkers were made for producing each plasmid. One linker homologously recombined with the 3' end of the digested plasmid and the 5' end of the Zalpha1 gene when transformed together with the digested plasmid and the Zalpha1 gene in *P. methanolica;* the second linker would homologously recombine with the 3' end of the Zalpha1 gene and the 5' end of the digested plasmid when transformed together with the digested plasmid and the Zalpha1 gene in *P. methanolica.*

Construction of the NEE-Zalpha1 Plasmid

The N-terminal-NEE-zalpha1 plasmid construct which produces Zalpha1 tagged with a Glu-Glu tag at the N-terminus, was made by recombining 100 ng of the SmaI digested pCZR204 acceptor vector, the 1 μl of the EcoRI-XhoI Zalpha1 cDNA donor fragment, the 1 μl of the N-terminal NEE-zalpha1 linker (SEQ ID NO: 35) and 1 μl of the C-terminal untagged linker (SEQ ID NO:36) in a *P. methanolica* transformation.

The NEE-zalpha1 linker was synthesized by a PCR reaction in which 4 picomoles of ZC13,497 (SEQ ID NO:28), 4 picomoles of ZC13,731 (SEQ ID NO: 29) 4 picomoles of ZC16,023 (SEQ ID NO:30 and 4 picomoles of ZC16,028 (SEQ ID NO:10) were placed in a PCR reaction mixture. The PCR mixture for the reaction further contained 40 μl of 10×PCR buffer, 8 μl EXTAG (both from Takara), 8 μl of 2.5 mM nucleotide triphosphate mix Takara) and 300 μl of water. The PCR reaction was incubated at 94° C. for 1.5 minutes, and then run for 10 cycles each individual cycle being comprised of 30 seconds at 94° C., 1 minute at 50° C. and 1 minutes at 72° C. The reaction was ended with an incubation for 10 minutes at 72°. This produced the oligonucleotide linker SEQ ID NO:35.

The C-terminal untagged Zalpha1 linker was made by placing 4 picomoles of ZC13,734 (SEQ ID NO:31) 4 picomoles of ZC15,633 (SEQ ID NO:32) 400 picomoles of oligonucleotide ZC16,025 (SEQ ID NO:33) and 400 picomoles oligonucleotide ZC16,027 (SEQ ID NO:34)in a PCR mixture identical to the above-described mixture and the PCR reaction was run under the same conditions as above. This produced the linker SEQ ID NO:36.

Construction of the CEE-Zalpha1 Plasmid

The N-terminal untagged Zalpha1 linker was made by mixing 4 picomoles of oligonucleotide (SEQ ID NO:37), 4 picomoles of oligonucleotide (SEQ ID NO:38), 400 picomoles of oligonucleotide (SEQ ID NO:39) and 400 picomoles of (SEQ ID NO:10) together in a PCR mixture identical to the above-described PCR mixture and running the PCR reaction as it was run above. This produced the linker of SEQ ID NO:40.

The C-terminal Zalpha1-CEE linker was made by mixing 4 picomoles of oligonucleotide (SEQ ID NO:41), 4 picomoles of oligonucleotide (SEQ ID NO:42), 400 picomoles of oligonucleotide (SEQ ID NO:43) 400 picomoles of (SEQ ID NO: 12) and 400 picomoles of (SEQ ID NO:13 together in a PCR mixture identical to the above-described PCR mixture and running the PCR reaction as was done above. This produced the linker of SEQ ID NO:44.

The C-terminal-CEE-Zalpha1 plasmid construct which expresses Zcyto10 tagged with a Glu-Glu tag at the C-terminus, was made by recombining 100 ng of the SmaI digested pCZR204 acceptor vector, the 1 μg of the EcoRI-XhoI zalpha1 cDNA donor fragment, 1 μl of the N-terminal untagged zalpha1 linker (SEQ ID NO: 40) and 1 μg of the C-terminal CEE-zalpha1 tagged linker (SEQ ID NO:44) in a *P. methanolica* transformation.

Construction of the Untagged Zalpha1 Expressing Construct

The untagged Zalpha1 expressing construct was made by recombining 100 ng of the SmaI digested pCZR204 acceptor vector, 1 μg of the EcoRI-XhoI Zalpha1 cDNA donor fragment, and 1 μg of each of the two recombinatorial linkers N-terminal untagged Zalpha1 oligonucleotide (SEQ ID NO:40) and the C-terminal untagged Zalpha1 oligonucleotid (SEQ ID NO:36) in a *P. methanolica* transformation.

Each N-terminal PCR-generated, double-stranded linker segment that spans 70 base pairs of the aFpp coding sequence on one end and joins it to the 70 base pairs of the amino-terminus coding sequence from the mature Zalpha1 sequence on the other. While each C-terminus linker contains about 70 base pairs of carboxy terminus coding sequence from Zalpha1 on one end with 70 base pairs of AUG1 terminator sequence. Ura+ colonies were selected, and DNA from the resulting yeast colonies was extracted and transformed into *E. coli*. Individual clones harboring the correct expression construct were identified by PCR screening followed by restriction digestion to verify the presence of the Zalpha1 insert and DNA sequencing to confirm the desired DNA sequences had been enjoined with one another. Larger scale plasmid DNA is isolated for one of the correct clones, and the DNA is digested with Sfi I to liberate the Pichia-Zalpha1 expression cassette from the vector backbone. The Sfi I-cut DNA is then transformed into a *Pichia methanolica* expression host, designated PMAD16, and plated on ADE D plates for selection. A variety of clones are picked and screened via Western blot for high-level Zalpha1 expression.

More specifically, for small-scale protein production (e.g., plate or shake flask production), *P. methanolica* transformants that carry an expression cassette comprising a methanol-regulated promoter (such as the AUG1 promoter) are grown in the presence of methanol and the absence of interfering amounts of other carbon sources (e.g., glucose). For small-scale experiments, including preliminary screening of expression levels, transformants may be grown at 30° C. on solid media containing, for example, 20 g/L Bacto-agar (Difco), 6.7 g/L yeast nitrogen base without amino acids (Difco), 10 g/L methanol, 0.4 mg/L biotin, and 0.56 g/L of -Ade -Thr -Trp powder. Because methanol is a volatile carbon source it is readily lost on prolonged incubation. A continuous supply of methanol can be provided by placing a solution of 50% methanol in water in the lids of inverted plates, whereby the methanol is transferred to the growing cells by evaporative transfer. In general, not more than 1 ml of methanol is used per 100-mm plate. Slightly larger scale experiments can be carried out using cultures grown in shake flasks. In a typical procedure, cells are cultivated for two days on minimal methanol plates as disclosed above at 30° C., then colonies are used to inoculate a small volume of minimal methanol media (6.7 g/L yeast nitrogen base without amino acids, 10 g/L methanol, 0.4 mg/L biotin) at a cell density of about $1\times10^6$ cells/ml. Cells are grown at 30° C. Cells growing on methanol have a high oxygen requirement, necessitating vigorous shaking during cultivation. Methanol is replenished daily (typically 1/100 volume of 50% methanol per day).

For production scale culturing, fresh cultures of high producer clones are prepared in shake flasks. The resulting cultures are then used to inoculate culture medium in a fermenter. Typically, a 500 ml culture in YEPD grown at 30° C. for 1–2 days with vigorous agitation is used to inoculate a 5-liter fermenter. The cells are grown in a suitable medium containing salts, glucose, biotin, and trace elements at 28° C., pH 5.0, and >30% dissolved $O_2$. After the initial charge of glucose is consumed (as indicated by a decrease in oxygen consumption), a glucose/methanol feed is delivered into the vessel to induce production of the protein of interest. Because large-scale fermentation is carried out under conditions of limiting carbon, the presence of glucose in the feed does not repress the methanol-inducible promoter.

We claim:

1. An isolated polynucleotide sequence comprised of SEQ ID NO: 1 or a portion thereof which encodes a polypeptide, said polypeptide being comprised of the amino acid sequence of SEQ ID NO:45 or SEQ ID NO:2.

* * * * *